United States Patent
Hess et al.

(10) Patent No.: US 8,057,036 B2
(45) Date of Patent: Nov. 15, 2011

(54) BINOCULAR VISION ASSESSMENT AND/OR THERAPY

(75) Inventors: Robert F. Hess, Montreal (CA); Behzad Mansouri, Winnipeg (CA); Benjamin Simon Thompson, Auckland (NZ)

(73) Assignee: McGill University, Montreal, Quebec (CA)

( * ) Notice: Subject to any disclaimer, the term of this patent is extended or adjusted under 35 U.S.C. 154(b) by 0 days.

(21) Appl. No.: 12/528,934

(22) PCT Filed: Oct. 23, 2008

(86) PCT No.: PCT/IB2008/054365
§ 371 (c)(1),
(2), (4) Date: Mar. 15, 2010

(87) PCT Pub. No.: WO2009/053917
PCT Pub. Date: Apr. 30, 2009

(65) Prior Publication Data
US 2010/0201942 A1 Aug. 12, 2010

Related U.S. Application Data

(60) Provisional application No. 60/987,078, filed on Nov. 11, 2007, provisional application No. 60/981,859, filed on Oct. 23, 2007.

(51) Int. Cl.
*A61B 3/08* (2006.01)
*A61B 3/00* (2006.01)
(52) U.S. Cl. ........... 351/201; 351/200
(58) Field of Classification Search ........... 351/200–246
See application file for complete search history.

(56) References Cited

U.S. PATENT DOCUMENTS

| | | | | |
|---|---|---|---|---|
| 5,309,185 A * | 5/1994 | Harper | .......... | 351/202 |
| 5,764,340 A * | 6/1998 | Hofeldt | .......... | 351/201 |
| 5,912,650 A * | 6/1999 | Carollo | .......... | 345/7 |
| 5,946,075 A * | 8/1999 | Horn | .......... | 351/246 |
| 6,851,807 B2 * | 2/2005 | Holdeman | .......... | 351/203 |
| 7,290,878 B1 * | 11/2007 | Hofeldt | .......... | 351/201 |

FOREIGN PATENT DOCUMENTS
DE 733 759 4/1943
(Continued)

OTHER PUBLICATIONS

McColl, et al., "Stereodeficient Subjects Demonstrate Non-Linear Stereopsis", Vision Research 40 (2000) 1167-1177, Elsevier Science Ltd., Montreal, Canada.

(Continued)

*Primary Examiner* — Mohammed Hasan
(74) *Attorney, Agent, or Firm* — Law Offices of Paul E. Kudirka

(57) ABSTRACT

An information difference between a left eye image and a right eye image is adjustable to achieve binocular vision in a patient having a deficiency of binocular vision. A source of image pairs is used along with a dichoptic display system to present a selected one of the image pairs as a right eye image to a patient's right eye and a left eye image to a patient's left eye. The difference at which a patients achieves binocular vision is a measure of a level binocular vision health or function, and continued exposure to the image pairs is therapeutic. The difference can be adjusted during therapy, and restoration of regular binocular vision is possible.

20 Claims, 17 Drawing Sheets

FOREIGN PATENT DOCUMENTS

| | | |
|---|---|---|
| EP | 0 578 236 A1 | 1/1994 |
| JP | 2006-122661 A | 5/2006 |
| WO | WO 96/27324 A1 | 9/1996 |
| WO | WO 03/092482 A1 | 11/2003 |
| WO | WO 2008/070683 A1 | 6/2008 |

OTHER PUBLICATIONS

Hess, et al., "Binocular Influences on Globarl Motion Processing in the Human Visual System", Vision Research 47 (2007) 1682-1692, Elsevier Science Ltd., Montreal, Canada.

* cited by examiner

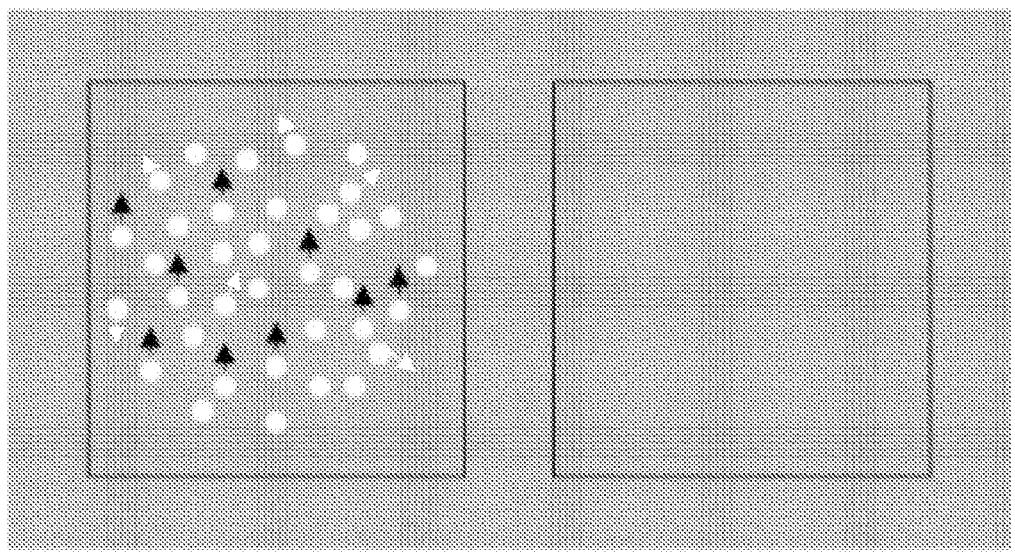
Figure 1A
Figure 1B
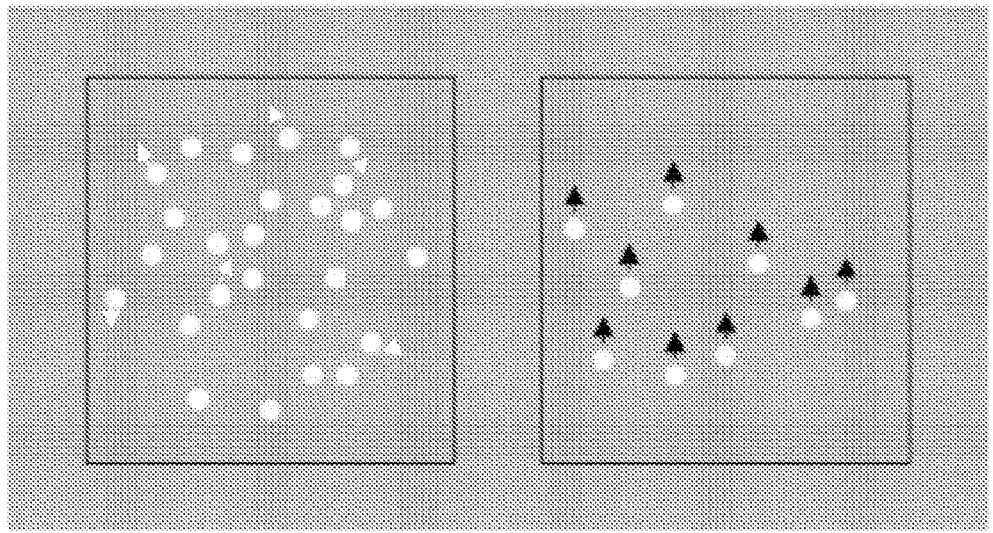

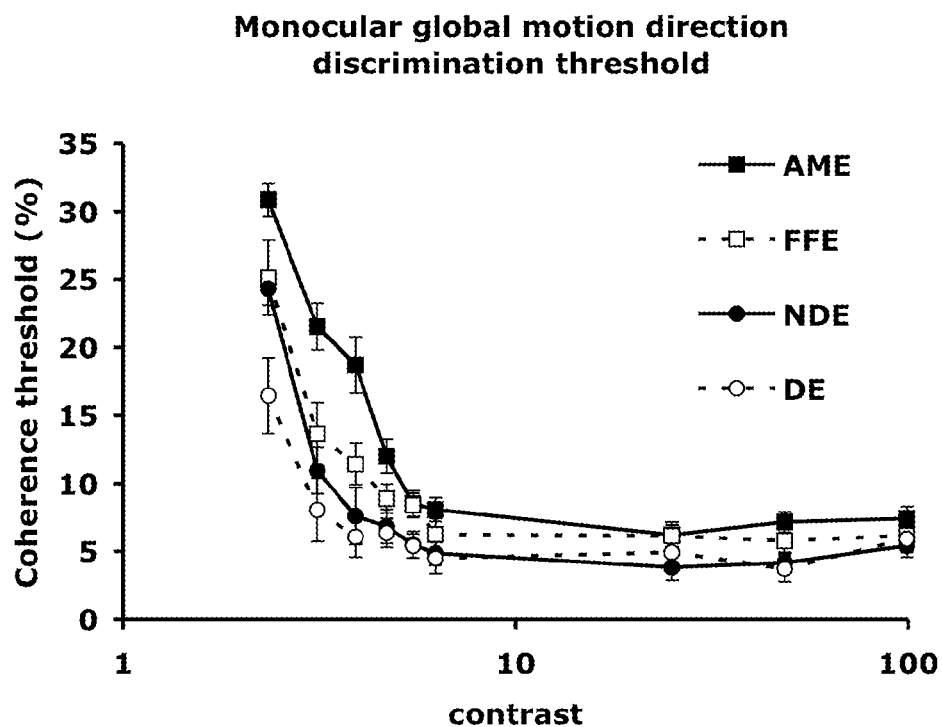
Figure 2A
Figure 2B
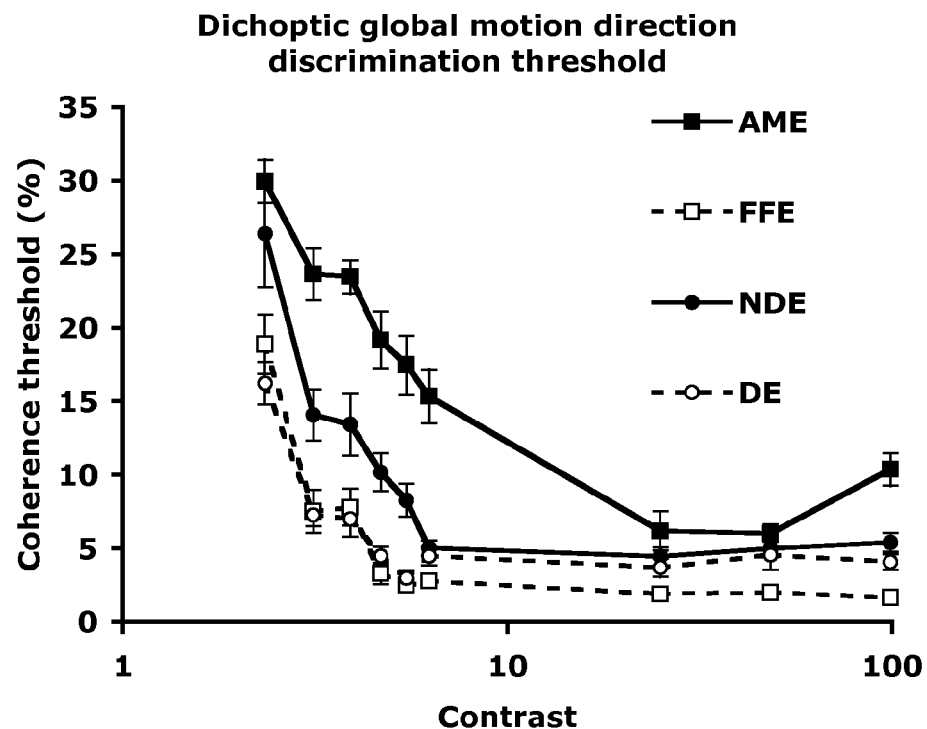

ED

GN

ML

ML

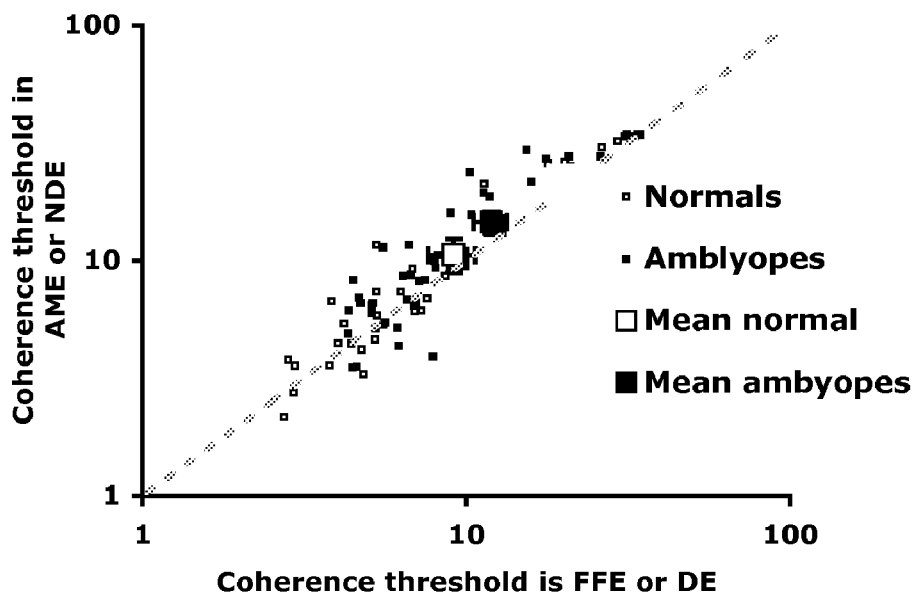
Figure 5A
Figure 5B
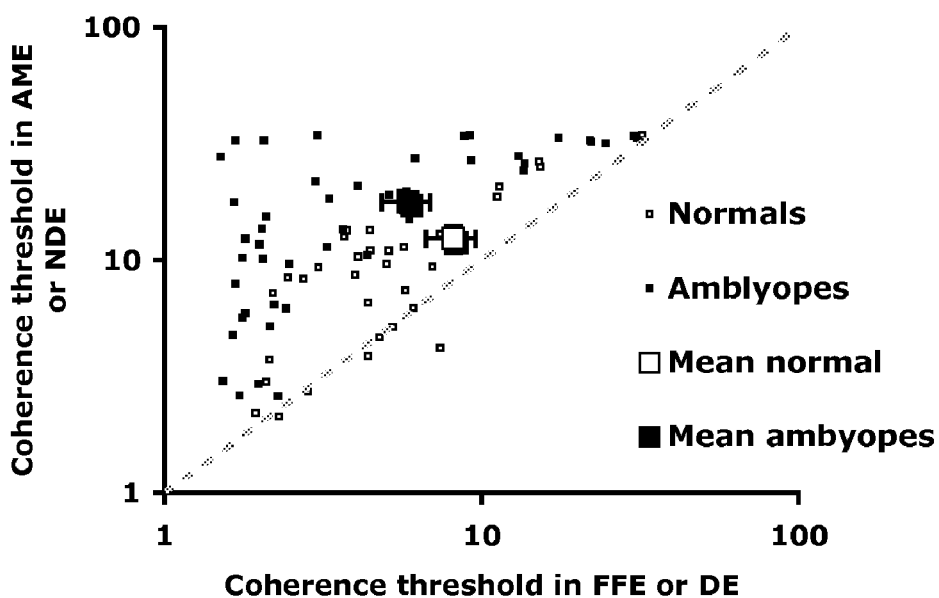

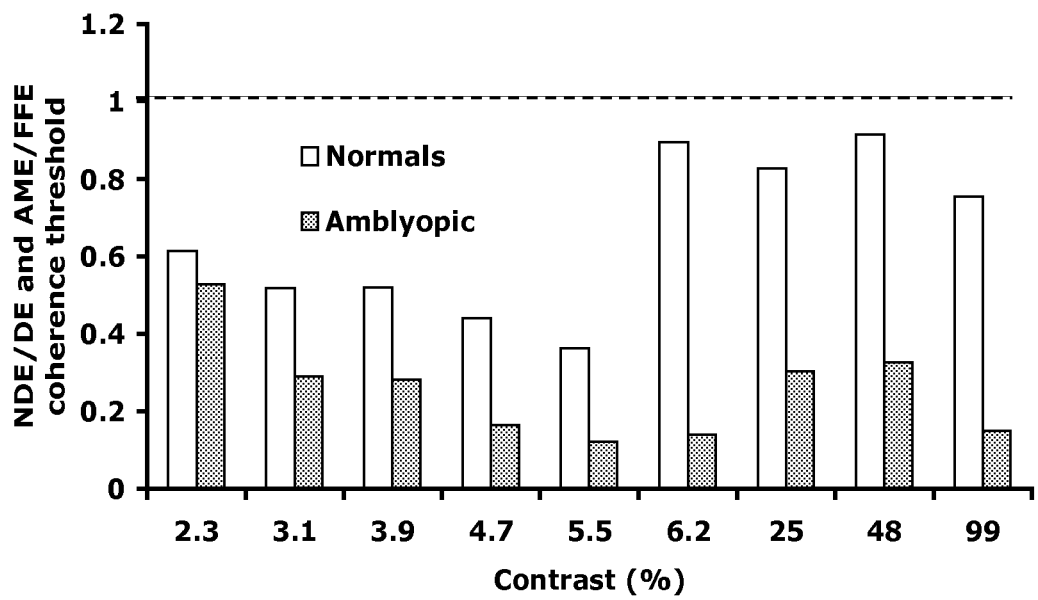
Figure 6
Figure 7A
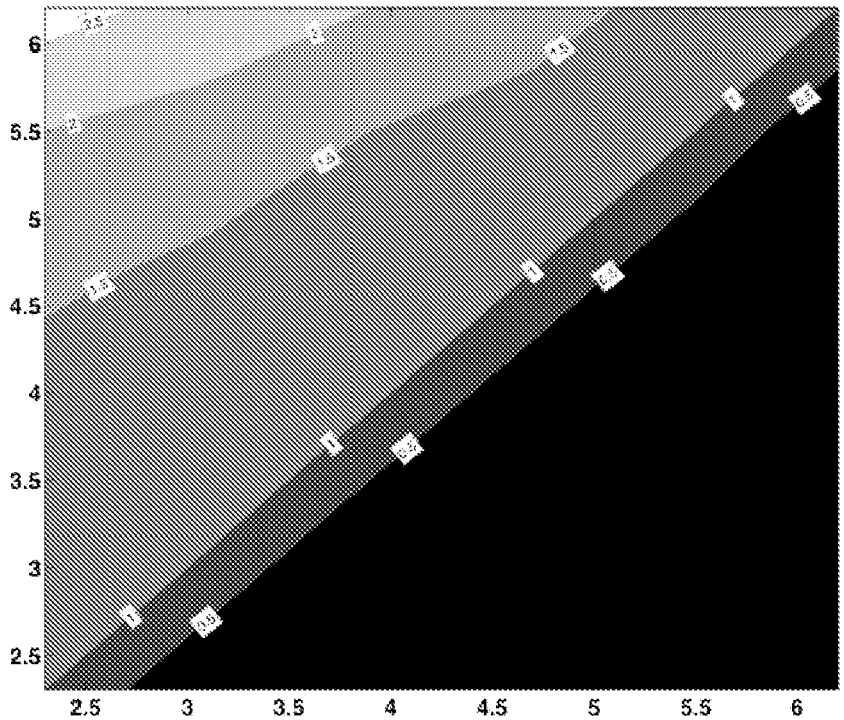

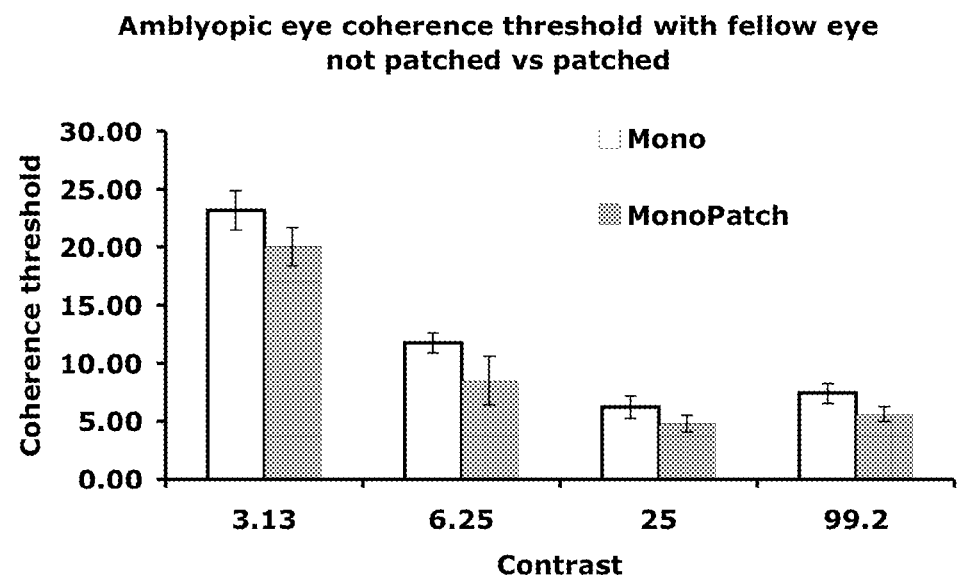
Figure 8
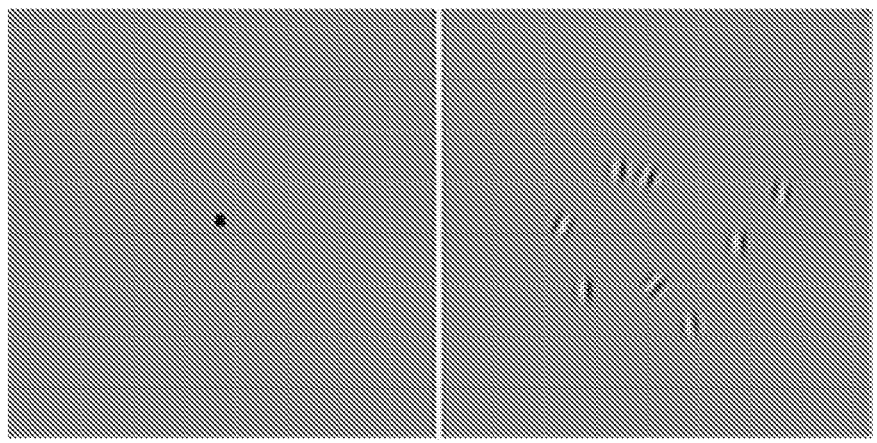
Figure 9A
Figure 9B
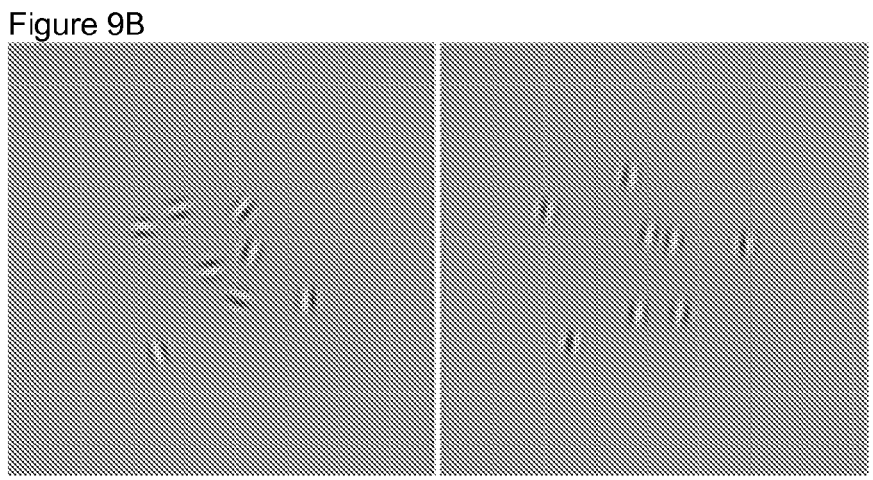

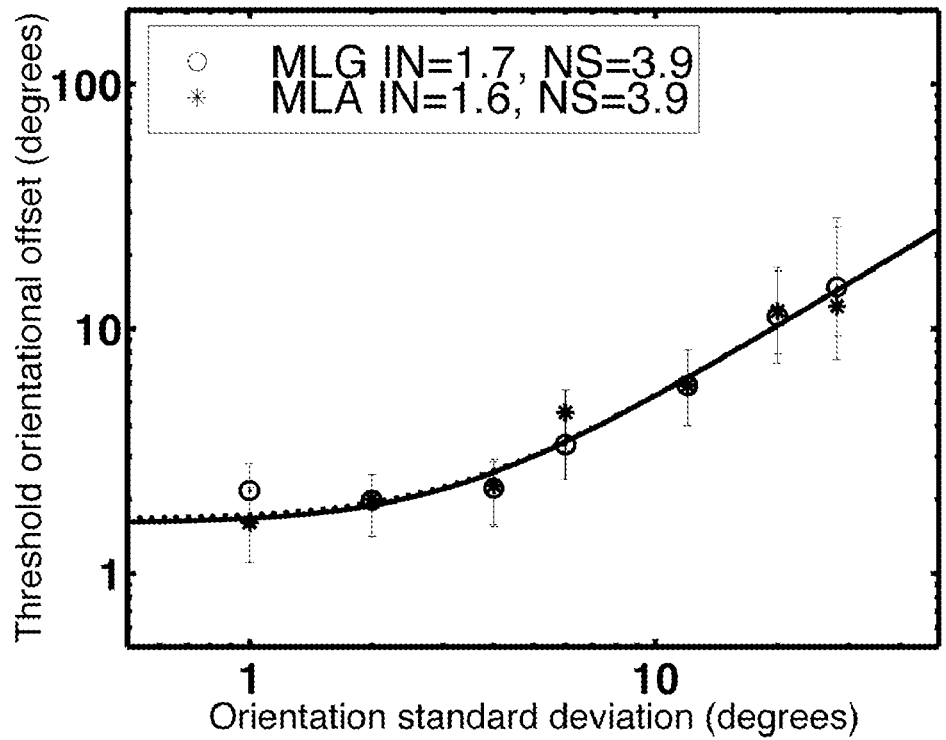
Figure 10
Figure 11A
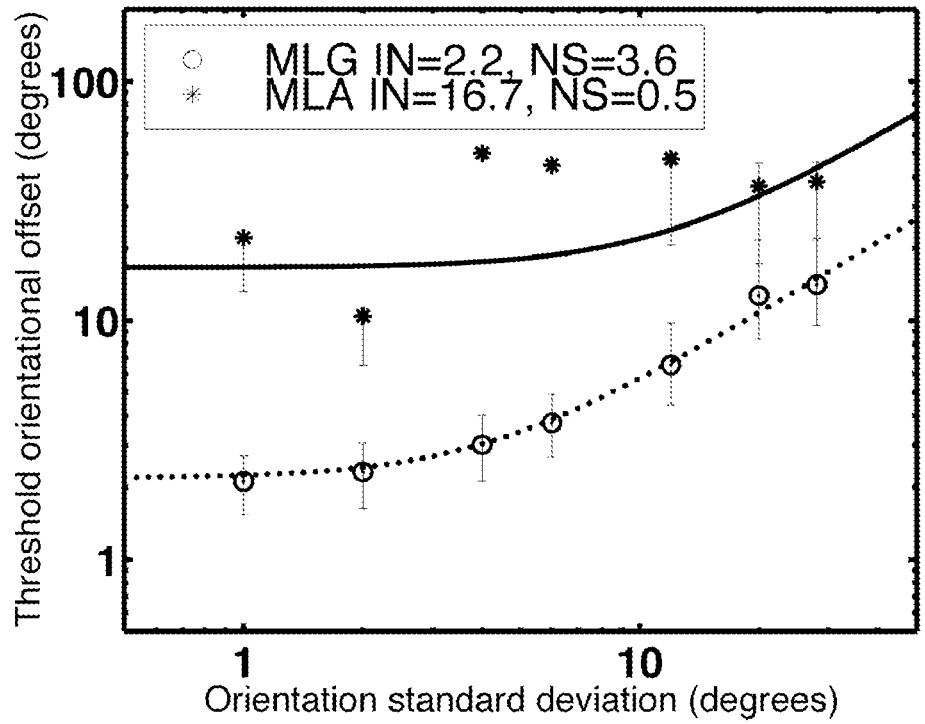

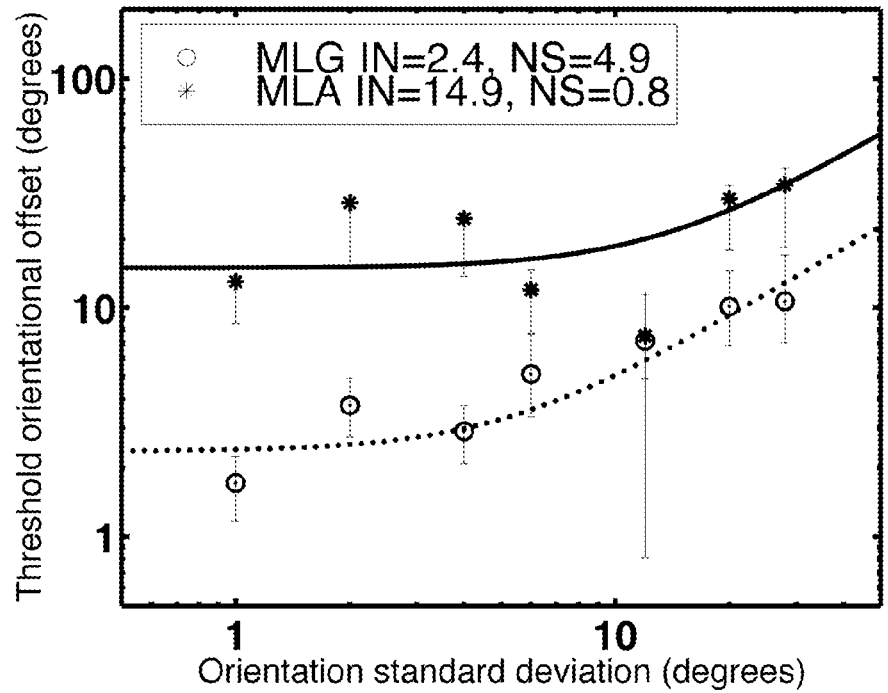
Figure 11B
Figure 11C
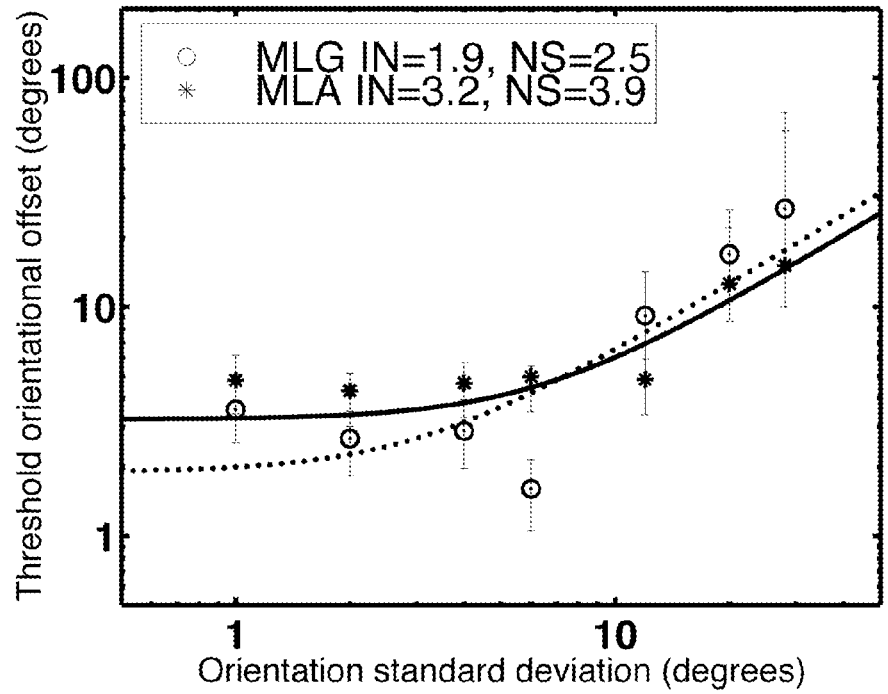

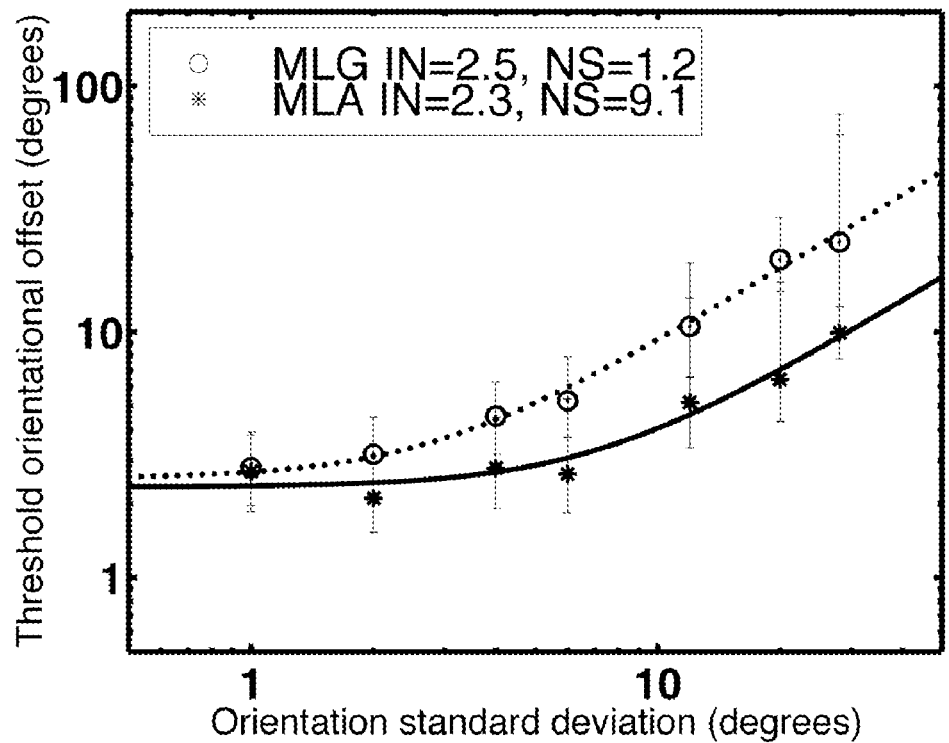
Figure 11D
Figure 12A
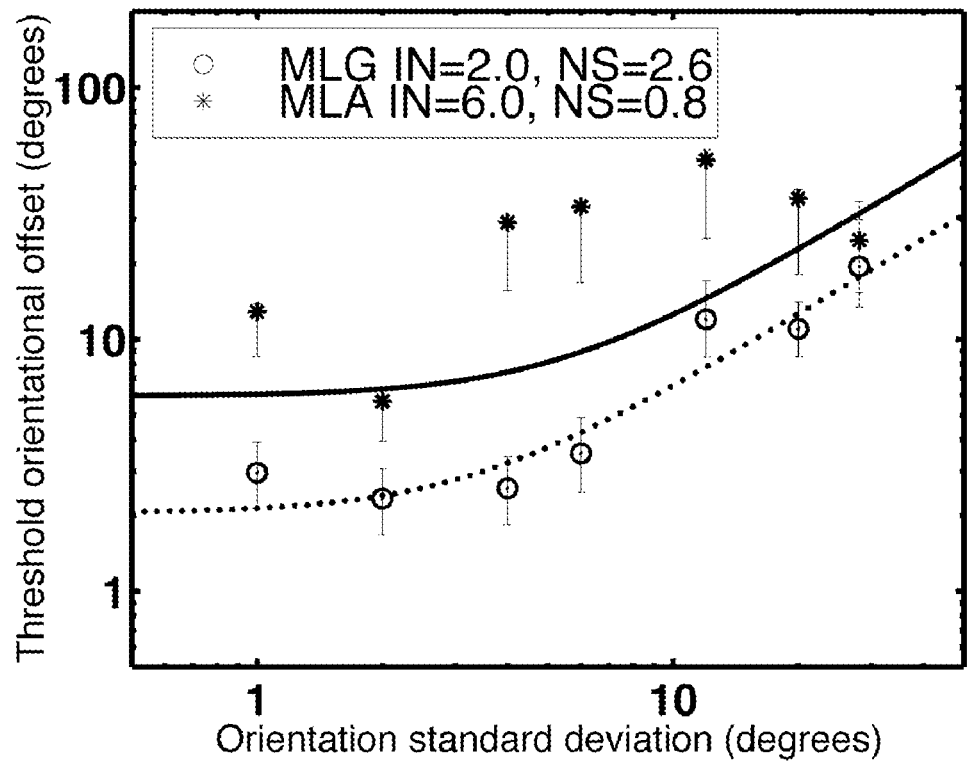

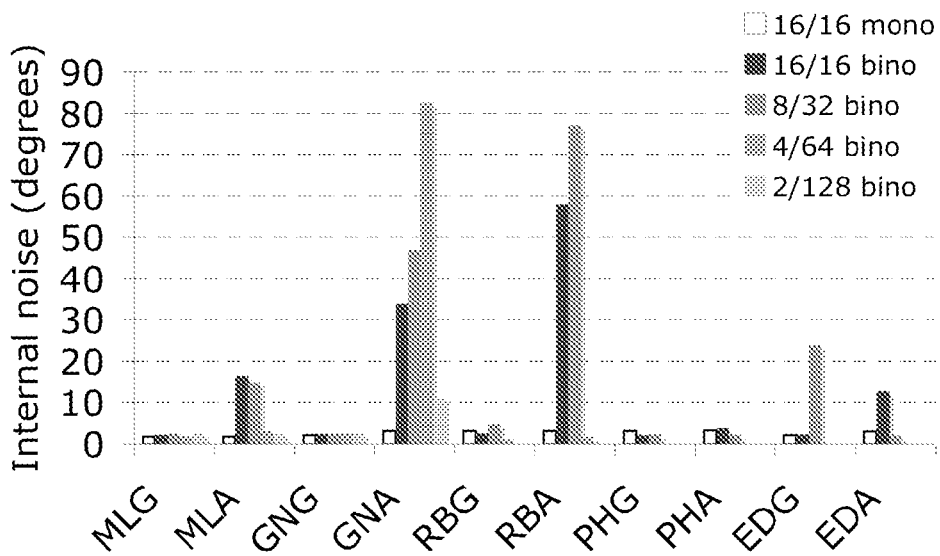
Figure 13A
Figure 13B
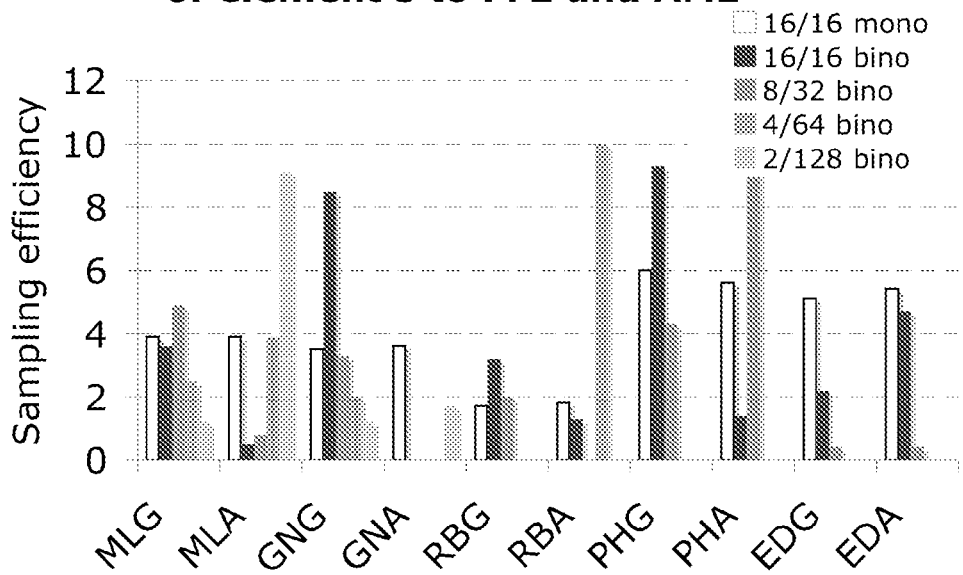

BINOCULAR VISION ASSESSMENT AND/OR THERAPY

TECHNICAL FIELD

The present invention relates to a method and to an apparatus for assessing and/or treating deficiencies in binocular vision.

BACKGROUND

Loss of binocular function is a common symptom of numerous visual disorders, which result in a loss of depth perception. Although there are many diverse causes of poor binocular function, the most extreme one is a condition called amblyopia, the world's most common cause of monocular blindness in adults. The health systems of many countries have, at great expense, developed screening programs to detect amblyopia in children, however when discovered, there is little that can be done to treat the problem. The amblyopic eye (AME) is subject to suppression from the fellow fixing eyes (FFE) whereby under binocular viewing conditions, information from that eye is not used. Treatments such as patching or penalizing the FFE have concentrated on improving monocular function of the amblyopic eye.

SUMMARY OF THE INVENTION

Applicants' approach is unique in that it first sets out to reduce the suppressive influences exerted by the fellow eye on the amblyopic eye under normal binocular viewing conditions so that the two eyes can work together. Applicants feel that the important issue in the treatment of amblyopia is the restoration of binocular function. Applicants' invention has been designed around the need to improve binocular function in amblyopia by first addressing the suppressive interactions between the eyes but it is applicable to any condition where the symptom is poor binocular function.

Applicants have discovered a way of activating the AME (or any weak eye) under binocular viewing conditions, a technique that could be highly beneficial for the treatment of amblyopia and other conditions in which a strong eye and a weak eye fail to work together properly, generally with impairment of binocular vision.

Applicants have also discovered a way of assessing a state of binocular vision health.

Applicants' invention concerns the measurement and treatment of monocular sensory visual loss associated with an unequal refractive error or a strabismus. Unlike previous inventions that are intended to passively aid the reduced vision of visually impaired patients (be they monocularly or binocularly impaired) by electronically enhancing images (U.S. Pat. No. 6,912,301 B1), Applicants' invention involves the measurement and active treatment of the suppressive influences that operate in patients with only one eye visually impaired. Prior art has addressed the measurement (EP 1 082 939 A2) and treatment (EP 0 830 839 A2; U.S. Pat. No. 5,936,126) of the muscular dysfunction underlying a strabismus. Applicants' invention does not address the muscular dysfunction but rather the sensory loss that is a separate entity and can occur in the absence of a strabismus. Prior art dealing with the sensory loss has used one of two approaches. In the first approach, the vision of the fellow good eye is occluded either physically or electronically (U.S. Pat. No. 6,511,175 B2; U.S. Pat. No. 5,264,877; U.S. Pat. No. 4,726,672; U.S. Pat. No. 5,452,026) with the goal of forcing the amblyopic eye to work. Applicants' invention does not involve the use of occlusion. The second approach involves binocular viewing of a scene where some extended image contours are seen exclusively by one eye and other extended contours, by the other (US 2006/0087618A1). In other words the images seen by either eye are spatially and/or temporally distinct, being different components of a composite image (eg clockface vs clock hands). This approach does not lend itself to a quantitative and valid measurement of the degree to which the different monocular images are combined binocularly and therefore cannot in itself guide treatment.

Applicants' invention does not utilize this approach. Although the apparatus separately displays right eye and left eye information (i.e. dichoptic display) this information must have comparable spatial or temporal (e.g. motion) properties calculated over the image as a whole. Furthermore, applicants adjust the strengths of the relative right eye/left eye information content to obtain a quantitative and valid measurement of the degree to which the different monocular images are combined binocularly. Applicants use a signal/noise approach where the information seen by one eye contains signal to accomplish the task at hand, whereas the information seen by the other eye contains noise designed to disrupt performance (i.e. signal/noise paradigm). The extent to which the noise seen by one eye disrupts performance gives a direct performance-related measure of how well information seen through that eye is combined with information seen by the other eye.

By information content applicants mean the overall luminance, local contrast, motion direction, motion speed, spatial sampling, spatial frequency and orientation of local image features. While the present approach uses a signal/noise paradigm it could be generalized to other stimuli where the information content of left and right images are systematically varied in a way that lends itself to a quantitative measure of the extent to which information from the two eyes are combined binocularly. Applicants model the combination of signal and noise in an analysis of the derived threshold performance and systematically adjust the balance of the information seen by each eye to obtain optimal binocular performance thresholds for the task. This gives a balance of information that a particular visual system can tolerate and a benchmark from which to gauge treatment progress. It supplies a valid measurement of the degree to which a stronger eye suppresses a weaker eye in cases of anomalous binocular vision. As a result of repeated measurements, the balance point gradually changes towards 50:50, which is the balance point in a normal individual with good binocular vision. Applicants use two different tasks based on the above principle to specifically target the functioning of the two major pathways carrying visual information in the extra-striate cortex, the ventral and dorsal pathways. Applicants use global spatial tasks to target the former and global motion tasks to target the latter.

Instead of patching a strong eye to exercise the weak eye, Applicants have discovered that the presentation of different images to both eyes can stimulate binocular vision. The different images may contain different information content, with the strong eye receiving less information than the weak eye.

The information content difference between the images presented at which a patient begins to experience binocular vision is an indication of the degree of binocular vision health. The treatment begins with an initial measurement of the degree to which the information content of the left and right images needs to be imbalanced for binocular combination to take place. This is called the balance point and represents a measure of the degree of interocular suppression. A training regime of duration between 1-2 hours is commenced such that images are presented with informational imbalances at and near to the previously measured balance point and psychophysical performance is monitored at these balance points for the task, be it motion direction discrimination or orientational discrimination. At the end of this training session, the balance point is re-measured using the same stimuli and tasks. If the balance point reading remains stable for 3 such treatment sessions, further treatment is discontinued. If the balance point reading reduces, further treatment is planned and this assessment/treatment cycle continues until the balance point value reaches an asymptotic value, signified by three consecutive balance values that are statistically indistinguishable. The assessment of the balance point is made by a clinically trained eye-care professional whereas the treatment may be implemented in a portable take home device whose performance related measures will be stored and able to be accessed subsequently by the eye care practitioner.

A variable difference between a left eye image and a right eye image is adjustable to achieve binocular vision in a patient having a deficiency of binocular vision. A source of image pairs is used along with a dichoptic display system to present a selected one of the images pairs as a right eye image to a patient's right eye and a left eye image to a patient's left eye. The variable difference at which a patient achieves binocular vision is a measure of a level binocular vision health or function, and continued exposure to the image pairs is therapeutic. The variable difference can be adjusted during therapy and restoration of regular binocular vision is possible.

Information content can take a variety of forms. Contrast, overall luminance, sampling, resolution, filtering, temporal, motion, orientation and contour are all examples of image characteristics that affect information content as perceived by the human brain. Some of these image characteristics can only be altered by image processing, while others may be altered by physical filters. Processed images having the desired information content difference can be recorded or stored for later display, or computer generated as required. Binocular vision can be experienced in patients having loss of or diminished binocular vision due to a strong eye/weak eye imbalance using images having information content difference with respect to one or more of these image characteristics. Preliminary results show that the amount of difference at which binocular vision is experienced can be different for different image characteristics.

The information content difference is selected or adjusted until a patient or user experiences binocular vision. This stage is useful for assessment of binocular vision health, and when continued, restores aided binocular vision and exercises the weak eye while forcing both eyes to work together. To improve binocular vision and work toward restoring unaided binocular vision, the information content difference is reduced, typically very gradually, with the goal of improving the ability for both eyes to work together.

BRIEF DESCRIPTION OF THE DRAWINGS

The invention will be better understood by way of the following detailed description of a preferred embodiment, with reference to the appended drawings, in which:

FIG. 1: Schematic presentation of the random dot kinematogram is shown for monocular (A) and binocular (B) conditions. Black arrows show the signal dots, which were moving, in the same direction (up vs down) within a trial. White arrows represent the noise dots, which were moving in random directions. In the monocular condition, signal and noise dots were presented to one eye at a time (A). In the binocular condition, signal and noise dots were presented to different eyes within each trial.

FIG. 2: Average contrast sensitivity threshold data for motion direction (exp. 1) for 7 amblyopic and 8 normal subjects is shown for amblyopic subjects' AME (solid line and filled squares) and FFEs (dashed line and open squares) and for normal subjects' non-dominant (solid line and filled circles) and dominant (dashed line and open circles) eyes for monocular (A) and binocular (B) conditions. The Y-axis represents the coherence threshold (%) in linear scale. The X-axis represents the contrast in logarithmic scale.

FIG. 5: Individual data points and average data for the coherence thresholds of the amblyopic and non-dominant eyes (filled squares) versus the fellow fixing and dominant eyes (open squares) are presented for monocular (A) and binocular conditions (B). The X-axis represents the coherence thresholds for the FFE and DE and the Y-axis represents the corresponding data for the AME and NDE. The dotted line shows the ratio of one line where the thresholds in two eyes would be the same.

FIG. 6: Average coherence threshold ratios for the non-dominant and dominant eyes in 8 normal observers and amblyopic and FFEs in 7 amblyopic subjects are presented at different stimulus contrasts. The X-axis represents the contrast (%) and the Y-axis represents the coherence threshold ratio for the amblyopic subjects (AME/FFE) (closed bars) and normals (NDE/DE) (open bars).

FIG. 8: A comparison of the performance of the AMEs under monocular conditions with patching of the FFE (closed bars) and without patching of the FFE, which saw mean luminance, instead (open bars) is presented. The X-axis is the percent contrast and the Y-axis is the coherence threshold (%). Error bars represent +/−1 SD.

FIG. 9: Schematic dichoptic mean orientation is presented for monocular (A) and binocular (B) conditions. In (A) only signal elements are presented to one eye and mean luminance plus fixation point to the other. In (B), signal elements are presented to one eye (right image in this presentation) and noise elements to the other eye (right image in this presentation).

FIG. 10: Mean orientation discrimination thresholds are presented for FFE (circles and dashed line) and AME (stars and solid line) for one amlyopic subject (ML). X-axis represents orientation standard deviation (°). Y-axis represents threshold orientation offset (°). Internal noise (IN) and sampling efficiency (NS) parameters which were derived from fitting the equivalent noise model to the data are presented in the inset. The contrast of the stimuli to FFE is 50% and to AME is 75%. At this combination of contrasts, the two eyes of this subject showed similar local orientation discrimination thresholds.

FIG. 11: Mean orientation discrimination thresholds are presented for FFE (circles and dotted lines) and AME (stars and solid lines) for AME/FFE number of elements ratio of 16/16, 32/8, 64/4, and 128/2 for A-D, respectively. Internal noise (IN) and sampling efficiency (NS) parameters are presented in insets. The X-axes represent orientation standard deviations (°). Y-axes represent threshold orientation offset (°).

FIG. 13: The internal noise (A) and sampling efficiency (B) is presented in this graph for 5 amblyopic subjects. One monocular condition (16/16) (open bar) and 4 binocular conditions (16/16 to 2/128) (from black to light grey) are presented for AME (A) and FFE (G) of the subjects.

DETAILED DESCRIPTION

Applicants applied techniques widely used in the study of higher level visual processing to the question of binocular vision in amblyopia. Specifically applicants used a classic signal/noise paradigm which applicants applied dichoptically, whereby signal was presented to one eye and noise to the other to assess binocular interactions in amblyopic observers. The rational was that if the eye receiving the signal was unable to process the information with which it was presented due to suppression, then only the noise presented to the other eye would be visible and the task associated with the signal population would be impossible. However if some information was available through the eye seeing the signal population, a behavioral measure of task performance would allow the applicants to quantify exactly how much information this eye was providing. Importantly, as the two populations of signal and noise were distinct, applicants were able to independently manipulate certain attributes of either population such as the contrast or the number of samples present in the population. In this way applicants were able to independently adjust the stimuli presented to each eye and to measure the contribution from each eye to binocular performance. Applicants found that under certain conditions where a reduced amount of stimulation was presented to the FFE and an enhanced amount to the AME, applicants could 'balance' the two eyes and measure behavioral responses clearly indicative of existing but weak binocular function in their amblyopic subjects. This was true for stimuli independently targeting either the dorsal visual processing stream (motion processing, experiment 1) or the ventral processing stream (form processing, experiment 2). Applicants were also able to precisely quantify the interactions between the two eyes by measuring the ratio of the difference between the two stimulus populations, e.g. the ratio of the contrast presented to the fellow eye vs. that presented to the AME.

Figure 15A:
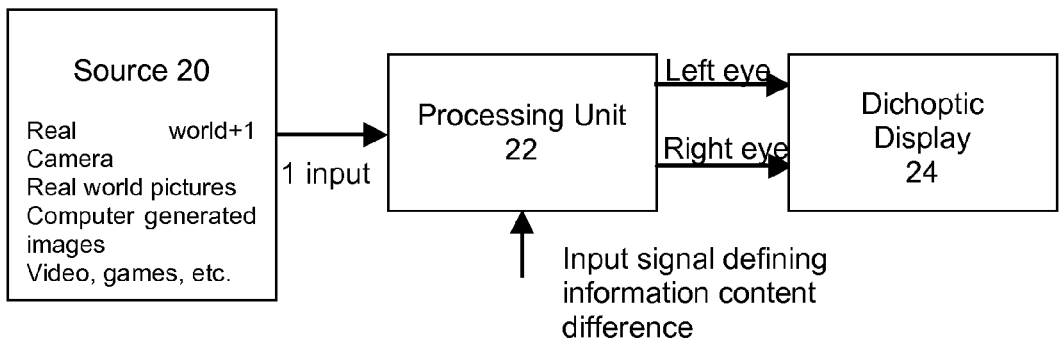
FIG. 15*a* is a schematic block diagram of a first embodiment of the invention in which a dichoptic monoscopic display is used.

Before describing the details of specific experiments, an overview of the basic apparatus according to two embodiments of the invention will be described with reference to FIGS. 15*a* and 15*b*, and the assessment and therapy using one embodiment of the invention will now be described with reference to FIG. 16. In the embodiment of FIG. 15*a*, an image source 20 comprises a camera or a computer image generator. The desired image is then processed by processor 22 in response to an input variable information content difference or ratio signal. In the case of a camera image, image filtering techniques (i.e. software) may be used to alter the information content, while in a computer generated image, selected image components may be selectively included or not in the different images. A dichoptic display system 24 is used by a user to view the images. A dichoptic display system is essentially a stereoscopic display system in which the displayed images are not different perspective images resulting in a 3D effect. Such display systems are well known in the art. It will be apparent to a person skilled in the art how to program a general purpose computer to provide a suitable user interface to control the adjustment of information content difference between right eye and left eye images displayed by the dichoptic display system.

Figure 15B:
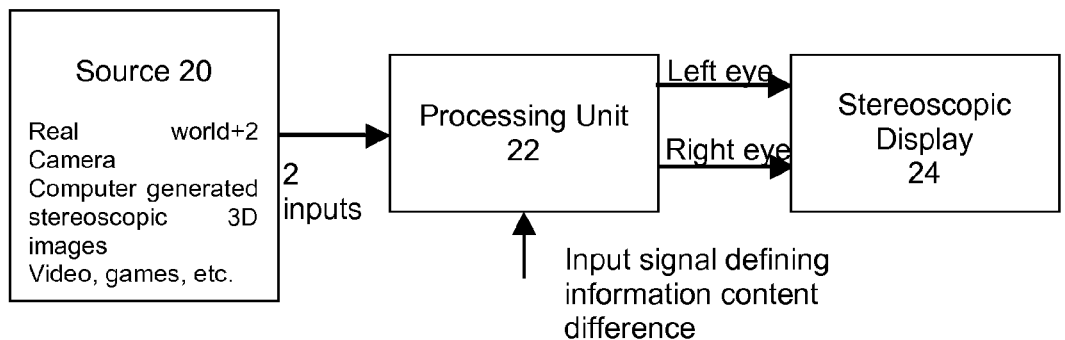
FIG. 15*b* is a schematic block diagram of a second embodiment of the invention in which a stereoscopic display is used.
Figure 15C:
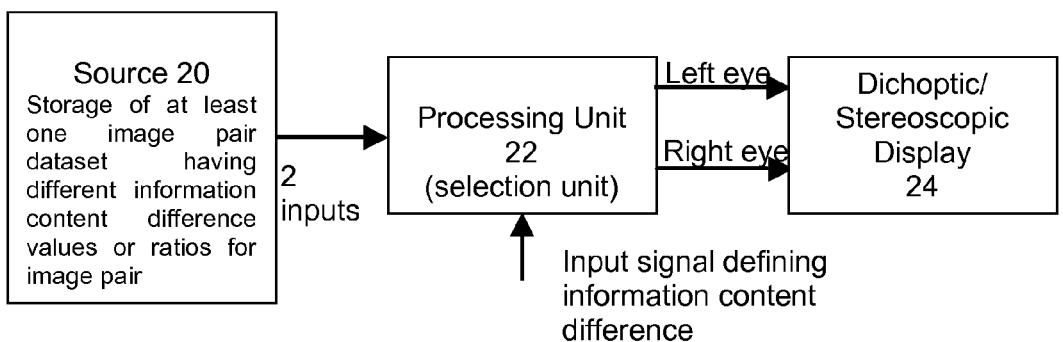
FIG. 15*c* is a schematic block diagram of a third embodiment of the invention in which the variable amount of information content difference is selected by selecting an appropriate image pair from a store of image pairs.
Figure 16:
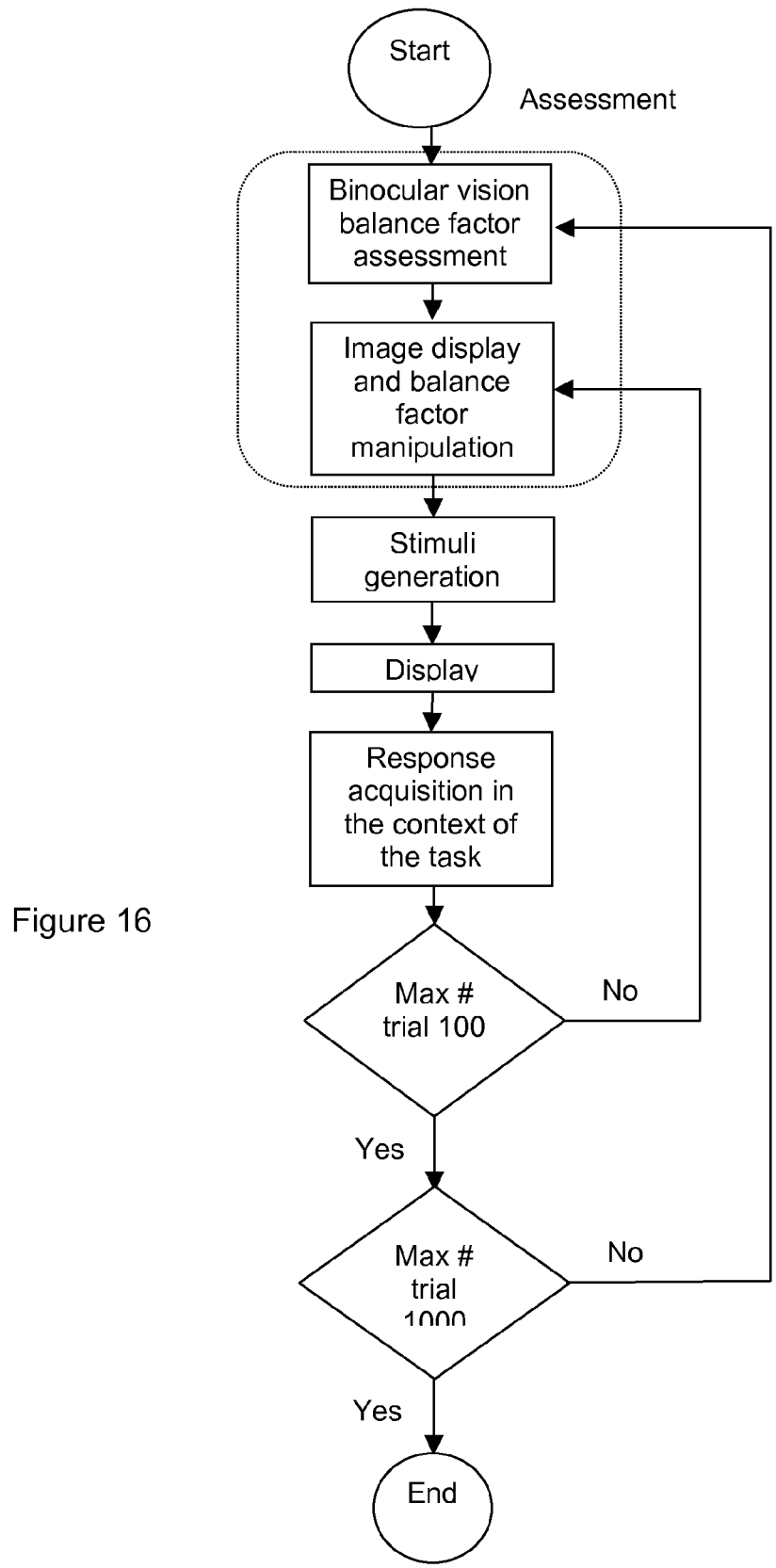
FIG. 16 is a flow chart of steps involved in a method of treating an amblyopic patient in one embodiment of the invention.

In the embodiment of FIG. 15*b*, the apparatus provides stereoscopic images, and thus the image source 20 is a stereoscopic image pair, and the image processor 22 alters the information content between the images, while respecting the different perspective information provided by the image pair. In the embodiment of FIG. 15*c*, the image source 20 is a store of at least one set of image pairs having a range of information content differences. As can be appreciated, the image store may contain tens, if not hundreds, of image pairs within a set, particularly when the information content difference is to be selected as a function of different image characteristics. In this embodiment, the image processor 22 is more of an image selection device that selects the appropriate image pair in response to the input desired difference signal. The image pair selected may be stereoscopic or not.

The apparatus of FIGS. 15*a* to 15*c* may comprise a general-purpose computer having suitable memory and data storage capabilities. The processor 22 may comprise suitable software executed by the computer, and the image source 20 may comprise the computer's data storage, a camera interface, a computer image generator program executed by the computer, or a suitable alternative, as will be appreciated by those skilled in the art. The video graphics electronics and software and display devices, including any shutter glasses, polarized lens glasses or prism glasses, that make up display 24 may involve components of a computer used for elements 20 and 22. A computer may also be programmed to provide a user interface for providing a user or operator with the ability to select the information content difference signal and other parameters, and additionally the interface may record user responses for analysis. The apparatus may also include a video game console or a personal computer equipped with video game software designed to allow for binocular separation of the visual information within the game either evenly or unevenly between the eyes. The display device may also incorporate technology to allow for an immersive virtual reality environment.

Therapy involves sessions of repeated image presentation, response acquisition and image modification. At the beginning, the binocular vision "balance factor" is assessed for each image attribute, using a task where the information from each eye is required. On the basis of the obtained "balance factor", image information content is modified, for example, images with reduced content information are presented to fellow eyes and images with augmented information content to the amblyopic eye, and responses are acquired in the context of the task. Feedback in the form of the task performance determines whether further modification of image content is necessary. After a number of repetitions binocular vision and stereovision are assessed. The aim is, through repeated trials, to affect a permanent change in the original balance factor in such a way that comparable information can be shown to each eye and used to obtain better performance on the dichoptic task. The training may also take the form of a video game either specifically designed for this purpose or modified by the image processing/display apparatus to facilitate training.

In an alternative embodiment, the apparatus comprises a user interface device in the form of a dial allowing the user to manually set the level of information content difference required in each eye for binocular vision. It is important for assessment and treatment of binocular vision deficiencies to perform all experiments above the threshold at which binocular vision is achieved. The dial allows continuous or step wise adjustments of information content such as overall luminance, local contrast, motion direction, motion speed, spatial sampling, spatial frequency and orientation of local image features. Another user interface device in an alternative embodiment can comprise computer screen user input objects, buttons, or stick (joystick) which allow the user to select an input during a task. For example in a motion determination task, the user selects one button when upward motion is perceived or another button when downward motion is perceived. In an orientation task, the user can select the orientation of gabors on a joystick, a dial or a series of buttons. Performance obtained by a user during any such task can be recorded by the apparatus, the data can be analyzed by software on a computer and plotted to allow easy interpretation and evaluation of therapeutic success of the regimen.

Use of a computer and software to capture data, analyze data and present pertinent data to the eye specialist is a further aspect of the invention since the measurement information content to each eye which is performed before each series of tasks as well as the actual results of the previous task allows the eye specialist (or the computer and software) to follow the success of the treatment regimen and to adjust treatment protocol, frequency and duration accordingly. For a user with binocular vision deficiencies such as amblyopia, the information content presented to the weak eye is greater than that presented to the strong eye for binocular vision to be achieved and therefore the calculated balance factor, which is simply of ratio of information content of the weak eye over the information content to the strong eye, will be greater than 1. Therapeutic efficiency is reached when the balance factor approaches, or ideally reaches 1 (50:50 contribution of each eye to binocular vision). Treatments which consist of repeated tasks are stopped either when the balance factor reaches 1 or when several consecutive tasks do not lead to an improvement in binocular vision (i.e. a decrease in the balance factor).

In an alternative embodiment, the computer and software can use real world images and selectively blur information rich areas of the strong eye image in order to favor information content processing from the weak eye, thus contributing to the improvement of binocular vision.

In yet another embodiment, the apparatus can include specialized glasses that can be worn such as LCD glasses or shutter glasses. These glasses can be connected, wirelessly or not, to a computer which contains the software necessary to coordinate and run the binocular vision treatment regimen.
Experiment 1—Dorsal Pathway Binocular Interactions The dorsal visual processing stream is thought to deal predominantly with motion information (Wurtz & Kandel, 2004). Accordingly, to study the dorsal pathway, applicants used random dot kinematograms (RDKs) to assess the binocular function of this pathway in amblyopia. Applicants used a coherence motion task. These stimuli are typically constructed of two populations of moving dots. The 'signal' population all move in the same direction termed the 'coherent' direction. Conversely, the 'noise' population has no common motion direction as all the dots move in random directions. The ratio of signal to noise dots required to recover the coherent motion direction is called the motion coherence threshold. The measurement of motion coherence thresholds is a well studied paradigm with regard to global motion integration (Braddick, 1974; Newsome, Britten, Salzman & Movshon, 1990; Newsome & Pare, 1988). One additional benefit of this paradigm is that it also provides a measure of signal noise segregation.

Motion coherence stimuli provide two sources of signal and noise whereby integrating the former increases performance and integrating the latter disrupts performance. Therefore, by using these stimuli with signal and noise separated dichoptically, one can independently study the mechanisms responsible for combining information from two eyes and measure the contribution of each eye to overall visual perception.

Applicants reasoned that if signal dots were presented to the amblyopic eye (AME) and noise to the fellow fixing eye (FFE), then the ability to perceive the coherent motion direction would only be possible if the AME were able to overcome the suppression of the FFE. In addition applicants could ensure that the two eyes were functioning binocularly by measuring motion coherence thresholds, a measurement that is only possible if both signal and noise populations are contributing to the final percept.

Applicants found that under dichoptic presentation of the signal and noise with similar contrast, the coherence threshold was higher when signal dots were presented to the AMEs and noise dots to the fellow eyes comparing to when signal dots were presented to the FFEs and noise to the AME. The higher coherence threshold in the former condition suggests that less information from the AME is contributing to visual perception. However, increasing the number of signal dots presented to the AME, as part of coherence threshold measurement, the binocular visual system started to fuse the images from two eyes and so could perform the task. This finding suggests that presenting proportionally more signal dots to AME can compensate for its visual deficiency. Applicants also manipulated the contrast of the stimuli presented to each eye independently where applicants presented the stimuli to FFEs at lower contrasts than those presented to the AMEs. Applicants found that with a certain ratio of contrasts between the two eyes (less contrast to the FFE) the AME was able to participate in the task and binocular vision was achieved, which indicates that presenting stimuli with higher contrasts to the AME can also compensate for its deficiency. The exact contrast ratio varied on an observer to observer basis. Importantly however, it was not the same as the difference in monocular contrast thresholds for this task, whereby both signal and noise populations were presented to one eye at a time. This demonstrated that dichoptic presentation yielded a true measure of binocular interaction.

As a final control applicants also measured monocular coherence thresholds in the AME when the FFE was either patched or viewing mean luminance. This provided a measure of the level of suppression of the AME elicited just by having the FFE open.

Experiment 2—Ventral Pathway Binocular Interactions

In a separate but similar experiment, applicants applied the same idea of (a) signal/noise binocular integration and (b) manipulating the number of samples and contrast for dichoptically presented form (e.g. orientation) stimuli. Applicants used a global mean orientation discrimination task where a patch of oriented Gabors were presented to the observers and they were asked to make judgments about the mean orientation, specifically, whether it was tilted to the left or right of vertical (see Methods of (Mansouri, Allen, Hess, Dakin & Ehrt, 2004)). The orientations of the signal Gabors were randomly selected from a predetermined population with a specific mean and variance. The orientations of the noise Gabors were selected from a flat distribution. Similar to experiment 1, applicants reasoned that integrating signal Gabors improves performance whereas integrating noise Gabors disrupts the performance of the visual system. Applicants could objectively measure the contribution of either eye to visual perception, based on the eye to which signal or noise were presented. Applicants changed the contrasts under which applicants could obtain monocular matched performance for the AME and FFE of every individual subject as a baseline for this study. Applicants found that although both eyes could perform similarly when stimuli with matched contrasts were presented to each eye monocularly, when stimuli with similar contrasts were presented dichoptically, the AME could no longer contribute. Therefore the binocular system was inactive when presented with stimuli accounting for the monocular AME deficiency, were presented to two eyes. However, when weaker stimuli (i.e. less samples or less contrast) were presented to the FFE, the AME started to contribute to binocular vision.

The implication of these findings is that for both dorsal and ventral visual processing, binocular mechanisms in amblyopia, whilst weak, are intact. Therefore treatment approaches to amblyopia should directly address the strengthening of this binocular system to overcome the suppressive mechanisms acting upon the AME.

TABLE 1

| Obs | Age/Sex | Type | Refraction | Dev | LA | Squint | History, stereo |
|---|---|---|---|---|---|---|---|
| AS | 21/F | RE | Ø | | 20/160 | ET 15° | Detected age 4 y, patching at 4 y |
|    |      | LE strab | −0.5 | DS | 20/20 | | for 6 m, surgery at 7 y, no |
| AR | 47/M | RE | Ø | | 20/20 | ET 1° | Detected age 6 y, no patching, |
|    |      | LE strab | Ø | | 20/50 | | no surgery |
| ED | 43/F | RE | +0.5 | DS | 20/16 | ET 5° | Detected age 6 y, patching for |
|    |      | LE strab | +0.5 | DS | 20/63 | | 1 y, normal local stereovision |
| GC | 20/F | RE | Ø | | 20/20 | ET 1° | Detected age 7 y, patching for 1-2 y, |
|    |      | LE strab | Ø | | 20/50 | | No surgery |
| GN | 30/M | RE | +5.00− | 120° | 20/70 | ET 8° | Detected age 5 y, patching for |
|    |      | mixed | 2.00 | 75° | 20/20 | | 3 m, no glasses tolerated, 2 |
| JD | 21/M | RE | +4.00 | DS | 20/63 | ET 5° | Detected age 5 y, patching for |
|    |      | strab | +1.50 | DS | 20/16 | | 3 y, no surgery, 2/10 local |
| ML | 20/F | RE | +1.0−0.75 | 90° | 20/80 | ET 6° | Detected age 5 y, patching for 2 y |
|    |      | mixed | −3.25 | DS | 20/25 | | |
| PH | 33/M | RE | −2.0+0.5 | DS | 20/25 | ET 5° | Detected age 4 y, patching for |
|    |      | LE strab | +0.50 | DS | 20/63 | | 6 m, |
| RB | 49/F | RE | +3.25 | DS | 20/15 | ET 10° | Detected age 6 y, glasses since |
|    |      | LE strab | +4.75− | 45° | 20/40 | | 6 y, no other therapy, near |

Table 1 provides clinical details of the amblyopic observers participating in the experiment. The following abbreviations have been used; strab for strabismus, aniso for anisometrope, RE for right eye, LE for left eye, ET for esotropia, XT for exotropia, ortho for orthotropic alignment, sph for diopter sphere.

Methods

Observers

Eight amblyopic and eight normal observers participated in the two experiments (seven and five amblyopic subjects completed experiment 1 and 2, consecutively). Refraction in all observers was tested and corrected to best visual acuity. The "Declaration of Helsinki" was followed and informed consent was obtained from all observers before data collection.

Eye dominance: Eye dominance for normal subjects was assessed for each subject using a sighting test (Rosenbach, 1903). Six subjects were right eye dominant, two were left eye dominant.

Apparatus (Exp. 1)

Stimuli were generated using Macintosh G4 and presented on a gamma-corrected Sony professional Series P22f monitor with a refresh rate of 75 Hz. The mean luminance of the display was approximately 50 cd/m$^2$. The RDKs were presented within a circular window at the centre of the display, which subtended 12° at the viewing distance of 92 cm.

Stimuli (Exp. 1)

Global motion stimuli were translational random-dot kinematograms (RDKs). Dots were presented on a homogenous mid-grey background (mean luminance of 50 cd/m$^2$) that filled the entire circular display window. The luminance modulation (Michelson contrast) and hence the visibility of the dots could be varied by increasing the luminance of the dots, with respect to the background, according to the following equation:

$$\text{Dot luminance modulation} = (L_{dots} - L_{background})/(L_{dots} + L_{background}),$$

where $L_{dots}$ and $L_{background}$ are the dot and background luminance, respectively. The luminance of the dots could be varied in the range 0.004 to 0.33. Each RDK was generated anew immediately prior to its presentation and was composed of a sequence of 8 frames, which when presented consecutively produced continuous apparent motion. The duration of each frame was 53.3 ms, resulting in a total stimulus duration of 426.7 ms. Each image contained 100 non-overlapping dots (dot density 0.88 dots/° 2) and the diameter of each dot was 0.235°. At the beginning of each motion sequence, the position of each dot was randomly assigned. On subsequent frames, each dot was shifted by 0.3°, resulting in a drift speed, if sustained, of 5.9°/s. When a dot reached the edge of the circular display window it was immediately re-plotted in a random spatial position within the confines of the window.

Procedure (Exp. 1)

The global motion coherence level of the stimulus was manipulated by constraining a fixed proportion of 'signal' dots on each image update to move coherently along a translational trajectory and the remaining ('noise' dots) to move in random directions. The signal dots direction could be either upwards or downwards on each trial with equal probability.

Experiment 1A, Monocular Condition

Both Eyes Open

Using a stereopscope the stimuli were randomly presented to one eye at a time within each run with all measurements carried out monocularly (see FIG. 1A). The observer was not aware of which eye was seeing the stimulus. Global motion thresholds were measured using a single-interval, forced-choice direction-discrimination procedure. On each trial, observers were presented with an RDK stimulus in which the signal dots moved along an upward or downward trajectory. The observers' task was to identify whether the motion was upwards or downwards. Data-collection was carried out using an adaptive staircase procedure (Edwards & Badcock, 1995). The staircase varied the proportion of signal dots present on each trial, according to the observer's recent response history. The staircase terminated after eight reversals and thresholds (79% correct performance) were taken as the mean of the last six reversals. Each threshold reported was based on the mean of at least five staircases.

Fellow Fixing Eye Patched

In the previous condition, on every trial the stimuli were presented to one eye and background (i.e. mean luminance) to the other eye in a random order. The mean luminance to one eye did not carry any relative information to the purpose of the task, so it cannot theoretically contribute in the subjects' final decisions about the task (i.e. upward or downward motion). However, the light through the fellow eye could stimulate the retinal cells nonspecifically. In amblyopia where the balance of interaction between two eyes is disturbed, and any stimulation of the fellow eye can strongly grab the visual attention, mean luminance to the fellow eye might have had a detrimental effect on the AME performance due to suppression. In order to measure the effect of mean luminance to the fellow eyes when stimuli were presented to the AME, applicants also tested the subjects monocularly with the FFE occluded with a patch. The effect of mean luminance to the fellow eye on AME performance is especially interesting because most amblyopia studies use patching for monocular testing of the AME. If the difference between the mean luminance and no light conditions is significant, applicants should reevaluate the patching paradigm for monocular testing.

Experiment 1B, Dichoptic Presentation

In experiment 2 the RDKs were presented within two horizontally separated, circular display windows, each equidistant from the centre of the screen (see FIG. 1B). Images were viewed at a distance of 114 cm through a Wheatstone Stereoscope. Each circular window subtended 7° and to aid binocular fusion, each display region was surrounded by a rectangular frame.

Dots were presented on a homogenous mid-grey background. The luminance modulation (Michelson contrast) and hence the visibility of the dots could be varied independently in two eyes by increasing the luminance of the dots, with respect to the background in an identical manner to Experiment 1.

In Experiment 2, performance was measured for translational global motion under dichoptic viewing conditions. Each presentation contained two images (see FIG. 1). Previously, in the monocular viewing condition, the signal and noise were presented to one eye and a uniform grey field of mean luminance was presented to the other eye. In the dichoptic viewing condition, the signal was presented to one eye and the noise was presented to the other eye. Since applicants varied the contrast of the signal and noise independently, applicants were able to present stimuli with high contrast to the AME and low contrast to the FFE.

All measurements were carried out under dichoptic viewing conditions in an identical manner to that employed in experiment 1.

In all monocular and dichoptic viewing conditions, measurements were repeated with either the left eye or the right eye within the same run of trials. In this instance, performance was tracked and thresholds (79% correct performance) measured for each eye using a two interleaved adaptive staircase procedure. Each threshold reported is based on the mean of at least six staircases. For the monocular and dichoptic viewing conditions, the results for the left and right eyes were combined.

Results (Exp. 1)

FIG. 2 represents the average coherence threshold data for monocular (FIG. 1A) and binocular (FIG. 1B) conditions. In the monocular condition (A) amblyopic and FFEs showed higher thresholds than those of the normal eyes. However, at medium suprathreshold contrasts (e.g. 5-8%) the AMEs showed significantly higher than normal thresholds whereas the FFE threshold was close to those of the normal eyes. In the dichoptic condition (B) AMEs showed significantly higher thresholds at all contrasts tested. The normal eye average thresholds fall between those of the amblyopic and FFE at the higher contrasts suggesting that not only does the AME suffer from suppression from the FFE, but also that the FFE benefits from this phenomenon.

FIG. 3 shows the change in the ratio of the coherence thresholds in the fellow fixing and AMEs when they were independently presented with stimuli of different contrasts. Stimuli presented to the AMEs always had similar or higher contrasts compared to those presented to the FFEs. FIG. 3(A-D) represents data for 4 individual amblyopic subjects. When stimuli with the same contrast were presented dichoptically to both eyes, the thresholds were always higher in the AMEs meaning that when the stimulation to both eyes had the same energy, the AME was less efficient. However, increasing proportional contrast to the AME improved the performance of the AMEs to the extent that in most cases a sufficiently large contrast ratio provided motion coherence threshold ratios equal to 1 meaning that both eyes were performing equally. At higher proportional contrasts, the AMEs showed even better performance than the FFEs.

Figure 3A:
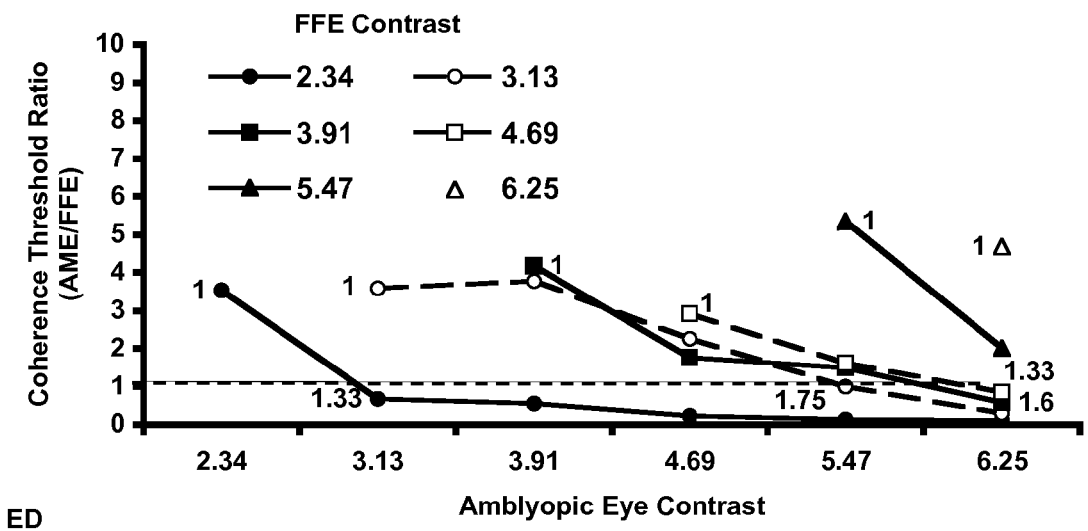
FIG. 3: Coherence threshold data for different combinations of contrasts to amblyoic and FFEs is represented for 4 individual subjects (A-D represent ED, GN, ML, and GC, respectively). The Y-axis represents the ratio of the AME to FFE coherence threshold. The X-axis represents the contrast of the stimuli, which were presented to the AME. The corresponding contrast of the stimuli presented to the FFE is presented as different curves (filled circle for 2.34%, open circle for 3.13% filled square for 3.91%, opened square for 4.69%, filled triangle for 5.475 and open triangle for 6.25%). The dotted line represents a ratio of 1 where the thresholds in both eyes are the same.
Figure 3B:
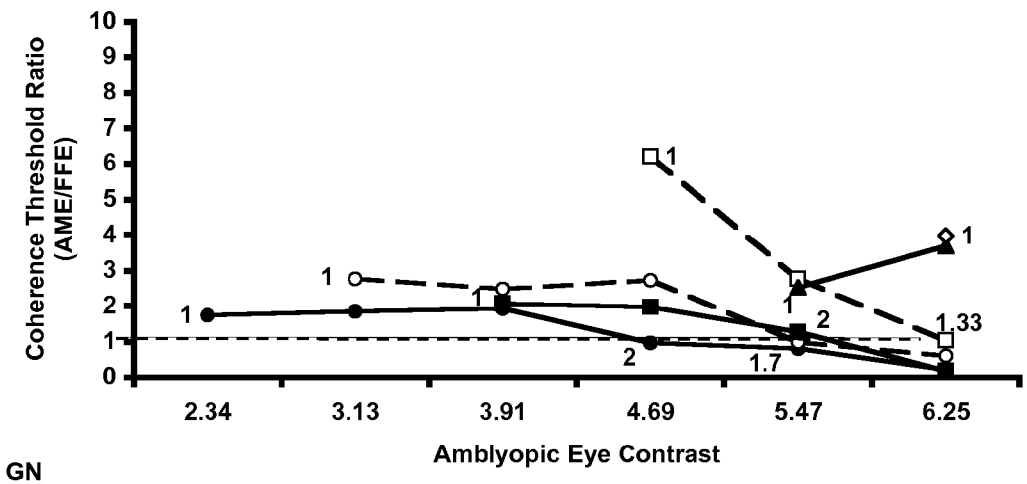
Figure 3C:
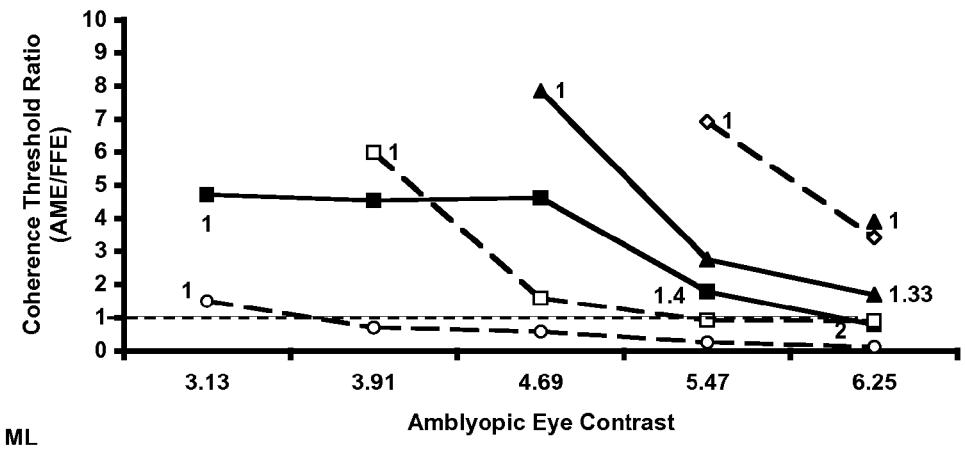
Figure 3D:
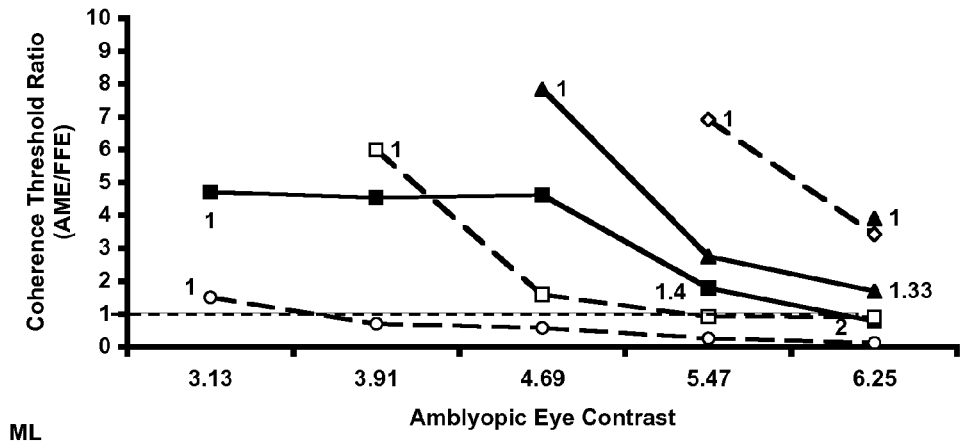
Figure 4:
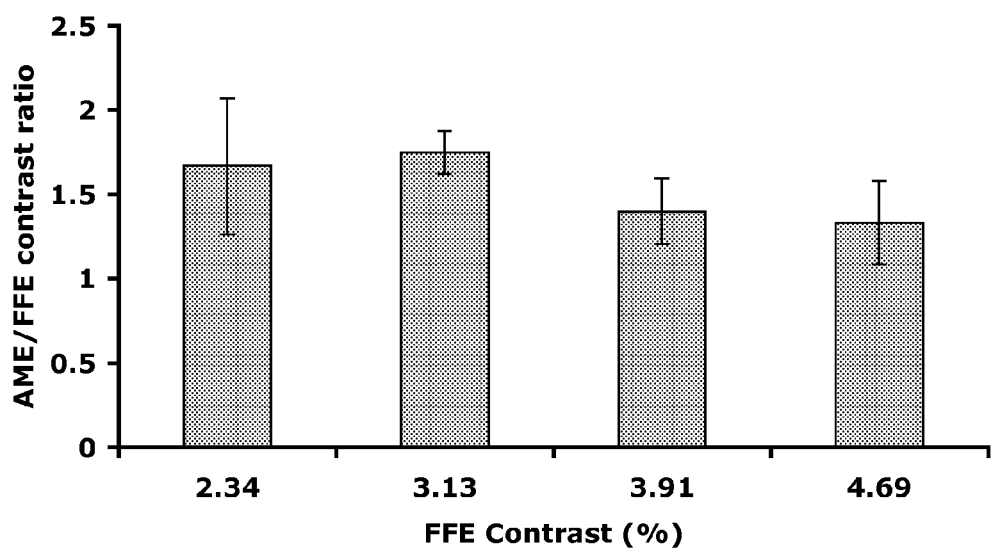
FIG. 4: The average contrast ratio of the fellow fixing to the AME when the coherence thresholds were equal in both eyes is presented in this figure. The X-axis represents the contrast of the stimuli to the FFEs and the Y-axis represents the contrast ratio of the stimuli to the AME and FFEs

FIG. 4 shows the ratio of the contrast of the stimuli presented to the AME and to the FFE when both eyes showed similar coherence thresholds. At all 4 different contrasts of the stimuli to the FFEs, AMEs needed more contrast (i.e. the ratio is higher than one) than the fellow eyes.

FIG. 5 shows the individual and average data for the amblyopic and non-dominant eye versus the corresponding value for the fellow fixing and dominant eye for monocular (A) and dichoptic (B) conditions. For the monocular condition most of the data points fall close to the dotted line (ratio of 1), although the filled squares (i.e. ratios for amblyopic subjects) are slightly higher than those of the normal subjects. This is also shown in the average data (i.e. big filled square versus big open square). However, the average for both data sets fall close to the dotted line which suggests that the FFEs and the AMEs are equally affected and have higher thresholds than those of the normal eyes.

For the binocular condition (B) however, the amblyopic data set is shifted up and to the left. The average data point for amblyopic subjects shows a shift to the left and above the average data point for the normal eyes. This suggests that the AME is much more defective than the FFE when those data are compared with those of the dominant and non-dominant eye.

FIG. 6 shows the average data for coherence threshold ratio in normal subjects' NDE over DE and for amblyopic subjects' AME over FFE for the dichoptic condition. For high contrast stimuli (e.g. over 6%) the ratio for normal subjects is close to one, which indicates a minimal difference in the performance of the DE and NDE at this range of contrasts. For AMEs however the differences in the performance of the AME versus the FFE is pronounced. At low contrasts (e.g. 3-5% contrasts) the AME difference remains constant but the normal eye differences decrease. At very low contrasts (e.g. below 3%) the NDE and AME show an almost similar deficit relative to the DE and FFE respectively.

Figure 7B:
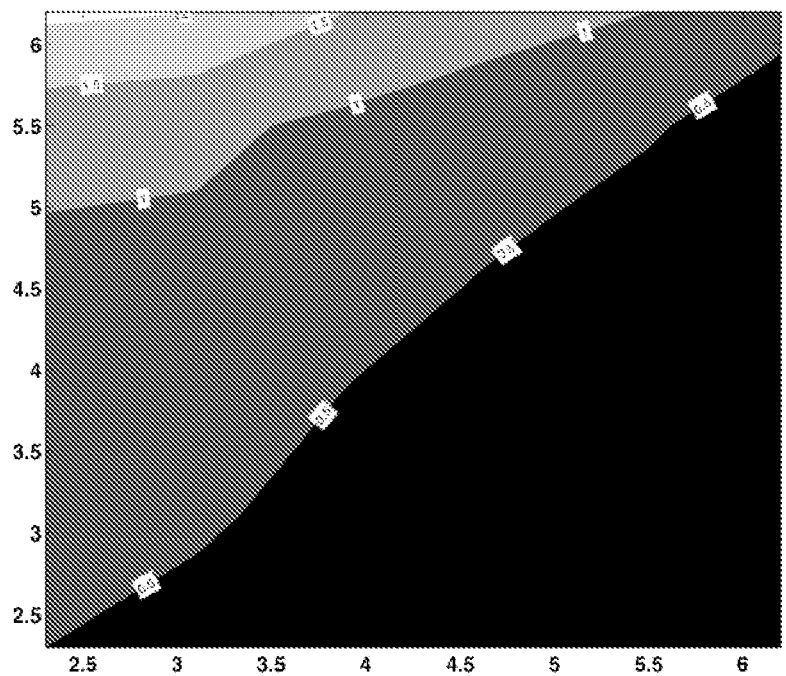
FIG. 7: The coherence threshold ratios of the AME over FFE for combinations of stimuli with different contrasts are presented for an ideal observer (A), monocular (B), and dichoptic (C) conditions. The X-axis represents the contrast of the stimuli to the FFE and the Y-axis represents the contrast to the AME. In (C) the average coherence threshold ratio of NDE to DE for normal observers for the dichoptic condition is represented on gray squares positioned along the diagonal axis where the contrasts of the stimuli were the same for both eyes.
Figure 7C:
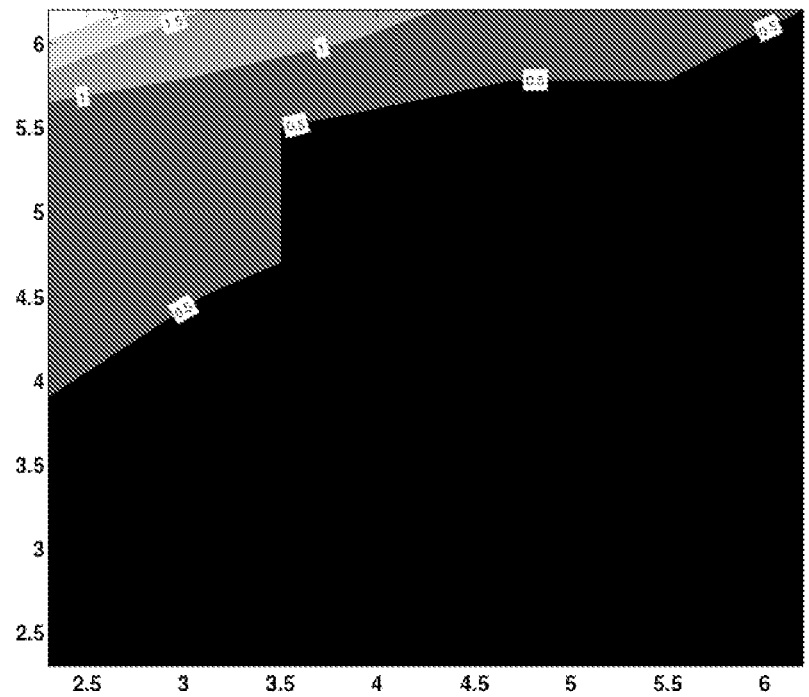

In FIG. 7 the coherence threshold ratios for the AME and FFE are presented with stimuli having different contrasts from a limited range (i.e. 2.5-6.5%). In (A) the data for an ideal observer is presented with the assumption that the information from the two eyes is linearly combined. The coherence thresholds are similar when the contrast of the stimuli to both eyes is the same and so the diagonal axis shows threshold ratios of one. Stimuli with higher contrast to either eye change the threshold ratio to the favor of that eye. In and monocular condition for amblyopic subjects (B) on the diagonal axis, where the contrasts of the stimuli to both eyes are the same, the ratios are 0.5 (on average), which indicates that the performance of the FFEs is twice as good as that of the AMEs. For equal performance (i.e. a ratio of one) the AME needs almost twice the contrast of that given to the FFE (e.g. 5 versus 2.5) to obtain similar performance. The amount of higher contrast required for similar performance of the two eyes decreases when the contrast to the FFE increases, however, there is a region of higher contrasts to the AME and lower contrasts to the FFE that provide similar performance for the two eyes. FIG. 7C shows the same plot as FIG. 6B, but for the binocular condition. The data shows that the curves are shifted up and therefore in order to have equal performance in two eyes, the AME needs much more contrast (5.7 versus 2.5). The average data for normal subjects under similar contrasts for both eyes is presented in grey squares along the diagonal axis. Unlike the ideal observer which has the ratio of one for corresponding thresholds from two eyes at the same contrasts, normal observers show better performance for DEs compared to NDEs when both are presented with the stimuli with the same contrasts. However the amblyopic subjects' ratios are dramatically higher than normals. Regarding the amblyopic subjects' data, there is still a region where the performance of the two eyes is similar under dichoptic presentation. There are even regions where the AMEs have better performance. This finding opens up a new opportunity for the treatment of amblyopia where under dichoptic presentation conditions, the AME can be activated.

In FIG. 8 the AMEs monocular performances are presented for when the FFEs are patched (open bars) and not patched (closed bars). The performance of the AMEs when FFEs are patched is better than when FFEs are open and presented with mean grey background. This is very important because it shows patching the FFE during psychophysical experiments slightly improves the vision in the AME and so partially conceals the AME deficiencies.

Experiment 2—Ventral Pathway Binocular Interactions

The results of experiment 1 indicated that binocular systems relating to dorsal visual processing are intact in amblyopia. As will be discussed in the following section, the treatment implications for this finding are significant. However any treatment targeting binocular function in amblyopia would not be satisfactory if only dorsal visual functions could be addressed. Applicants therefore applied the same dichoptic signal/noise paradigm to ventral stream processing in amblyopia. In Experiment 2, rather than motion information, applicants used small visual tokens (Gabor patches) each of which contained information at a specific orientation. One eye was presented with a signal population within which the orientation of each Gabor was randomly chosen from a population with predetermined mean and variance. The other eye was presented with a noise population within which each token had a random orientation. The task was to indicate the 'signal' orientation. With the same logic applied to Experiment 1, applicants reasoned that if the AME were presented with signal and the fellow eye with noise, complete suppression of the AME would lead to an inability to perform the task as only noise information would be available. However if any information from the AME was available to conscious perception, the amount of information could be objectively measured using psychophysical task performance. As in Experiment 1 applicants were able to independently manipulate the properties of each population of Gabors to control either the contrast or the physical number of Gabors presented to each eye (the 'number of samples'). Applicants found that the amblyopic visual system once again demonstrated intact binocular vision when either the contrast to the FFE was reduced, the number of samples was altered in favor of the AME or a combination of both. Once again the relative ratio of the information presented to each eye could be considered as an objective measure of binocular function in amblyopia that could not be predicted based on monocular differences in performance.

Apparatus (Exp. 2)

A Power Macintosh G3 computer was used to generate and display the stimuli. Stimulus presentation was controlled by the Matlab environment (MathWorks Ltd) and Psychophysics Tool Box (Brainard, 1997). All stimuli were displayed on a 20-inch Sony Trinitron GDM-F520 monitor for the disparity and control experiments. The monitor was calibrated and linearized using a Graseby S370 photometer and the Video Toolbox (Pelli, 1997) package. Pseudo 12 bit contrast accuracy was achieved by using a video attenuator (Pelli & Zhang, 1991) which combined the RBG outputs of the graphic card (ATI Rage 128) into the green (G) gun. The refresh rate was 75 Hz. The mean luminance of the screens was 28 cd/m². The resolution was 1152×870 pixels. One pixel on the screen was 0.32 mm, which was 2.12 arcmin of the observers' visual angle from the viewing distance of 52 cm.

Stimuli (Exp. 2)

Separate stimuli were presented to the left and right eyes, using a mirror stereoscope. Each eye viewed an independent image. These images were 6°×6° wide and arranged on the screen centrally and adjacent to each other. The left and right eye images were fused into one cyclopean image by the observer. Stimuli were arrays of Gabor micro-patterns presented on a 30° (height)×38° (width) (from the observers distance) mean luminance background. The envelope of each Gabor had a standard deviation of 0.4 degree of visual angle.

The spatial frequency of sinusoidal modulation within the Gabors was 0.52 cycles per degree (cpd). Typically, 16 Gabors were presented to each eye. These were positioned randomly within a circular area inside the box outline, centered on the center of the box. When the patches overlapped (as could occasionally occur), their gray levels were added, if this led to brightness levels outside the possible luminance range, they were clipped appropriately at the maximum or minimum contrast values.

The orientation of each Gabor was controlled by its parent distribution. Two types of parent distribution were used, producing two different Gabor populations: 'noise' and 'signal'. The orientation of each Gabor micro-pattern in the signal population was selected from a Gaussian distribution with a mean equal to the orientation cue (i.e. 90°±the cue generated by APE, an adaptive method of constant stimuli (Watt & Andrews, 1981) and a variable bandwidth. The distribution's standard deviation, $\sigma_{ext}$, was varied from 0° (all elements aligned) to 28° (high orientation variability). The orientations of Gabors in the noise population were selected from a Gaussian distribution with a standard deviation of 90°. Applicants used the same method to generate the parent distribution of the noise Gabors as were used to generate the parent distribution of the signal array. This meant that the noise population distributions had a randomly selected (on each trial) mean orientation, however, given the breadth of the distribution this was not discernable. Note also that since orientation is a circular variable (i.e. any orientation beyond 180° or below 0° is equivalent to its equilibrium in the 0° to 180° range), Applicants' noise populations were equivalent to uniform distributions between 0 and 180 degrees. Two different combinations of signal and noise were tested. Depending on which condition was tested, each eye's image could contain a signal population, a noise population or both. A stereoscope was used to show the left image to the left eye and the right image to the right eye. To prevent any bias, the observers were not informed which population (e.g. signal or noise) was being presented at any time and if different Gabor populations were presented to different eyes, the process was randomized within a run so that observers were unaware of which stimulus was presented to which eye. Observers did not receive feedback.

Two combinations of signal and noise were:

Signal population presented to FFE/DE and mean luminance to the AME/NDE, and vice versa (FIG. 9A).

Signal population presented to FFE/DE and noise population to the AME/NDE, and vice versa (FIG. 9B).

As stated above, all subjects started the experiment with the signal and noise populations each comprised of 16 Gabors and continued with different proportions of signal and noise and different contrast ratios for stimuli to either eye.

Procedure (Exp. 2)

A single temporal interval two alternative forced choice paradigm was used. The observers' task was to judge whether the mean orientation of the array of Gabors was rotated clockwise or counter-clockwise (tilted to right or left of vertical) (see FIG. 1). The stimulus presentation time was 500 ms in the main experiment. On each trial, observers indicated their decision with a button press. The mean orientation of the signal population was controlled by APE, an adaptive method of constant stimuli (Watt & Andrews, 1981) which sampled a range of orientations around vertical. Given that thresholds are estimates of response variance, the non-ideal behavior of observers with noiseless stimuli can be expressed as an additive internal noise. The level of internal noise is measured by increasing the amount of external noise in the stimulus and determining the point at which observers' performance begins to deteriorate. If the task requires integration, then observers' robustness to increasing amounts of external noise will depend decreasingly on internal noise and increasingly on how many samples are averaged. Thus the form of the equivalent noise model is:

$$\sigma_{obs}^2 = (\sigma_{int}^2 + \sigma_{ext}^2)/n$$

Where $\sigma_{obs}$ is the observed threshold, $\sigma_{ext}$ is the external noise, $\sigma_{int}$ is the estimated equivalent intrinsic or internal noise and n is the estimated number of samples being employed. In terms of the orientation discrimination task, $\sigma_{obs}$ corresponds to the threshold for orientation discrimination, $\sigma_{ext}$ to the standard deviation of the distribution from which the samples are derived, $\sigma_{int}$ to the noise associated with the measurement of each orientation sample and their combination and n corresponds to the estimated number of orientation samples being combined by the visual system. It is important to note that this is an equivalent noise model and that the model supplies equivalent estimated parameters. This is especially important in the later section where oriented noise populations (randomly oriented Gabors) are combined with signal Gabor populations. Orientation discrimination thresholds were derived from between 192-340 presentations for each of a number of standard deviations of the parent distribution i.e. external noise (10 levels typically between 0-28°). The orientation threshold for each level of variance of the parent distribution was estimated as the slope of the best fitting cumulative Gaussian function using a maximum likelihood procedure in which the threshold was equal to 82% correct (King-Smith & Rose, 1997). 1000 bootstrap replications of the fitted function were carried out and used to generate 95% confidence intervals (Cis) for the threshold estimates (Foster & Bischop, 1997). The orientation discrimination thresholds at each level of external noise were fitted by the equivalent noise model to derive the measures of internal noise and number of samples.

Results (EXP. 2)

FIG. 10 shows a condition where signal is presented to one eye at a time and mean luminance to the other eye (see FIG. 9(A)). The contrasts of the stimuli to the FFE and AME are set at a level that induces similar performance for the two eyes at the level of local orientation discrimination (e.g. 50% contrast to FFE and 75% contrast to AME for this example subject). So clearly if the AME is compensated for its contrast deficiency at local orientation level, it can perform the mean orientation task similarly to the FFE in a monocular presentation condition.

FIG. 11(A-D) shows different numbers of elements, which were dichopticly presented to one amblyopic subject (ML). In (A), 16 signal Gabors are presented to FFE and 16 noise Gabors to AME (circles and dashed line) and visa versa (stars and solid line) at a similar combination of contrasts as presented in FIG. 10 (50% to FFE and 75% to AME). The performance of the FFE when noise was presented to the AME is similar to when no noise was presented to AME. This suggested that at this condition, the noise through the AME has little effect in disrupting the performance of the visual system. On the contrary, noise through FFE can completely disrupt the performance of the visual system when signal Gabors are presented to the AME. This is very interesting because both eyes showed similar performances when tested with similar stimuli but under monocular conditions (see FIG. 10). The disturbed performance of the AME is demonstrated by high thresholds as well as high levels of internal noise and lower sampling efficiency, as derived from fitting the equivalent noise model to the threshold data (see Methods). Internal noise parameters increased by a factor of 10 (i.e. 1.6 in FIG. 10, to 16.7) and sampling efficiency diminished from 3.9 to 0.5.

In FIG. 11(B) the number of elements to the FFE is reduced to 8 and to the AME increased to 32. Although this different number of elements slightly improved the performance of the AME, there was still a large difference in the performance of the two eyes. In some subjects such as ED, though, this ratio of different number of samples was enough to equalize the performance of the two eyes. In FIG. 11(C) the number of elements to the FFE is 4 and to the AME is 64. At this ratio, the performance of the two eyes in this individual subject were similar which is reflected in both the thresholds and the model parameters (IN=1.9 and 3.6 and NS=2.5, 3.9 in FFE and AME, respectively). This suggests that originally the visual system didn't combine the information, which was presented dichoptically to two eyes. Instead, the visual system ignored the AME even when it contained the useful information i.e. signal Gabors. However, when stronger information was presented to the AME, the visual system fused the images from the two eyes, which shows that the binocular system was activated. In FIG. 11(D) applicants pursued the process of increasing the number of elements to the AME whereby 128 Gabors were presented to the AME and 2 elements to the FFE. The performance of the AME continues to improve over that of FFE which is specially reflected in the high standard deviations and sampling efficiency (i.e. NS=1.2 and 9.1 in FFE and AME, respectively). Therefore the dominance of the FFE over AME is not absolute. It is possible to create artificial circumstances where the AME has dominance over the FFE.

Figure 12B:
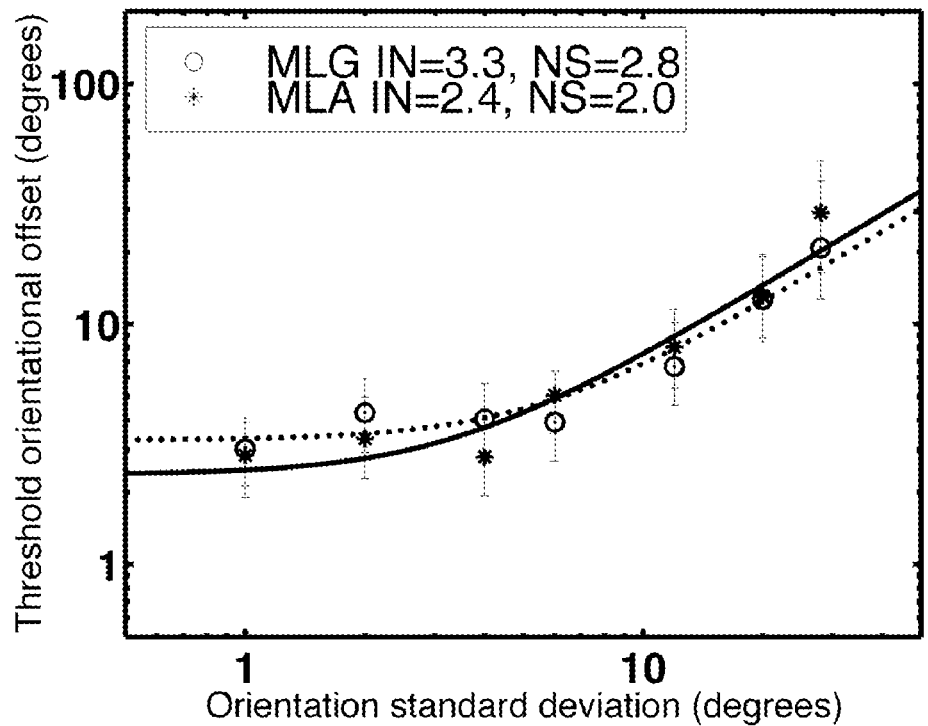
FIG. 12: Mean orientation discrimination thresholds are presented for FFE (circles and dotted lines) and AME (stars and solid lines) for AME/FFE contrast ratio of 75% to 25%, 75% to 10%, and 75% to 5% for A-C, respectively. Internal noise (IN) and sampling efficiency (NS) parameters are presented in insets. The X-axes represent orientation standard deviations (°). Y-axes represent threshold orientation offset (°).
Figure 12C:
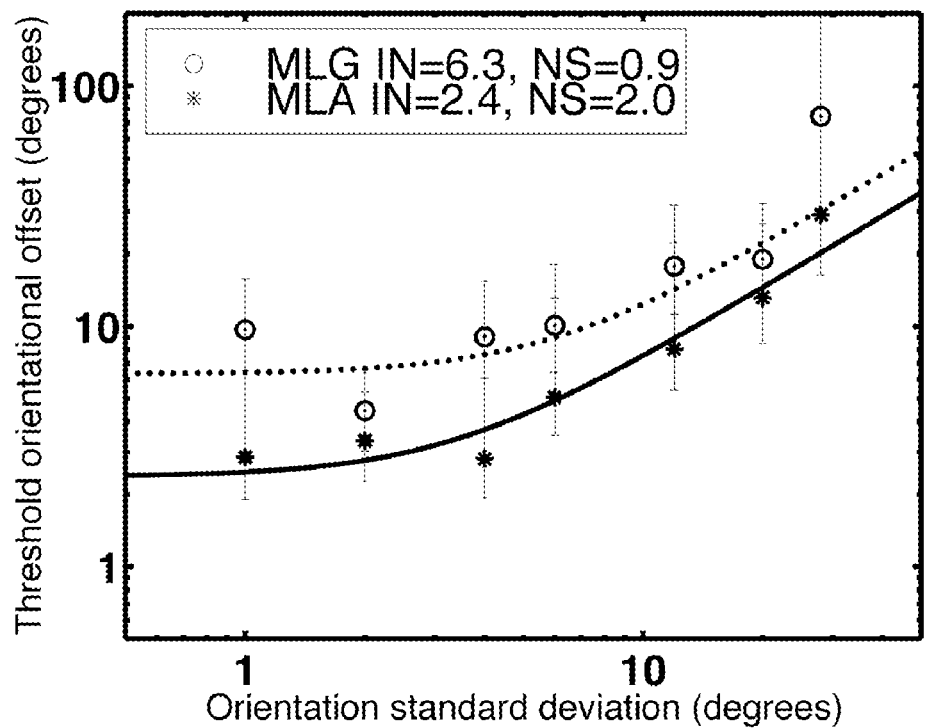

FIG. 12(A-D) shows conditions where the number of the stimuli to both eyes and contrast of the stimuli to the AME is kept constant (i.e. 16 Gabors and 75%, respectively) and the contrast of the stimuli to the FFE is reduced to 25% in A, 10% in B and 5% in C. Reducing the contrast to the FFE to 25% improves the performance of the AME (IN in AME equals to 16.7 in FIG. 11(A) when contrast of the stimuli to FFE is 50% compared to 6.0 in FIG. 12(A) when that is 25%). This suggests that there is an inhibition from the FFE over the AME (i.e. suppression) that can be reduced by reducing the relative contrast to the FFE. In (B), reducing the contrast of the stimuli to the FFE to 10% was enough to equalize the performance of the two eyes. Greater reduction in contrast of the stimuli to the FFE results in better performance of the AME compared to that of the FFE (IN=6.3 and 2.4 in FFE and AME, respectively (FIG. 12(C)).

FIG. 13 shows internal noise (A) and sampling efficiency (B) parameters in 5 amblyopic subjects who completed the condition where the number of elements was changing. Internal noise increased and the number of samples decreased dramatically in the amblyopic eyes when monocular presentation was changed to binocular presentation even when a similar number of elements were presented to the two eyes. The internal noise in FFEs however, did not change. When the ratio of number of elements presented to the AME to those presented to the FFE decreased, internal noise in the AME became closer to the internal noise in the fellow eye. The behavior of the sampling efficiency parameter was not consistent in all observers. Generally however, it decreased in AMEs for the binocular presentation condition. When the ratio of the number of elements presented to two eyes changed (i.e. decreased), the sampling efficiency changed accordingly and became closer to that of the FFEs.

Figure 14A:
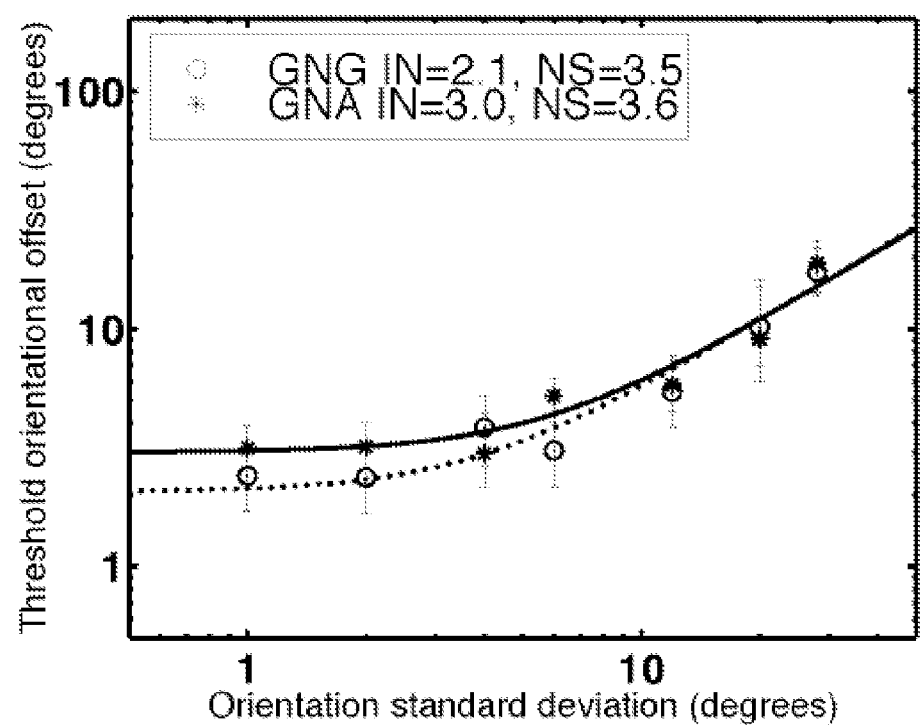
FIG. 14: The mean orientation discrimination thresholds for one amblyopic subject (GN) is presented for matched contrast monocular condition (A) and combinations of different number of elements and contrasts to AME and FFE (B). In (B) the number of elements changes from 16/16 to 2/128 along the horizontal axis and the contrast from 25/75 to 5/75 along the vertical axis. Combinations of changes in number of elements (i.e. FFE/AME from 16/16 to 2/128) and contrast (FFE/AME from 25/75 to 5/75) brought the performance of the AME and FFE close to each other.
Figure 14B:
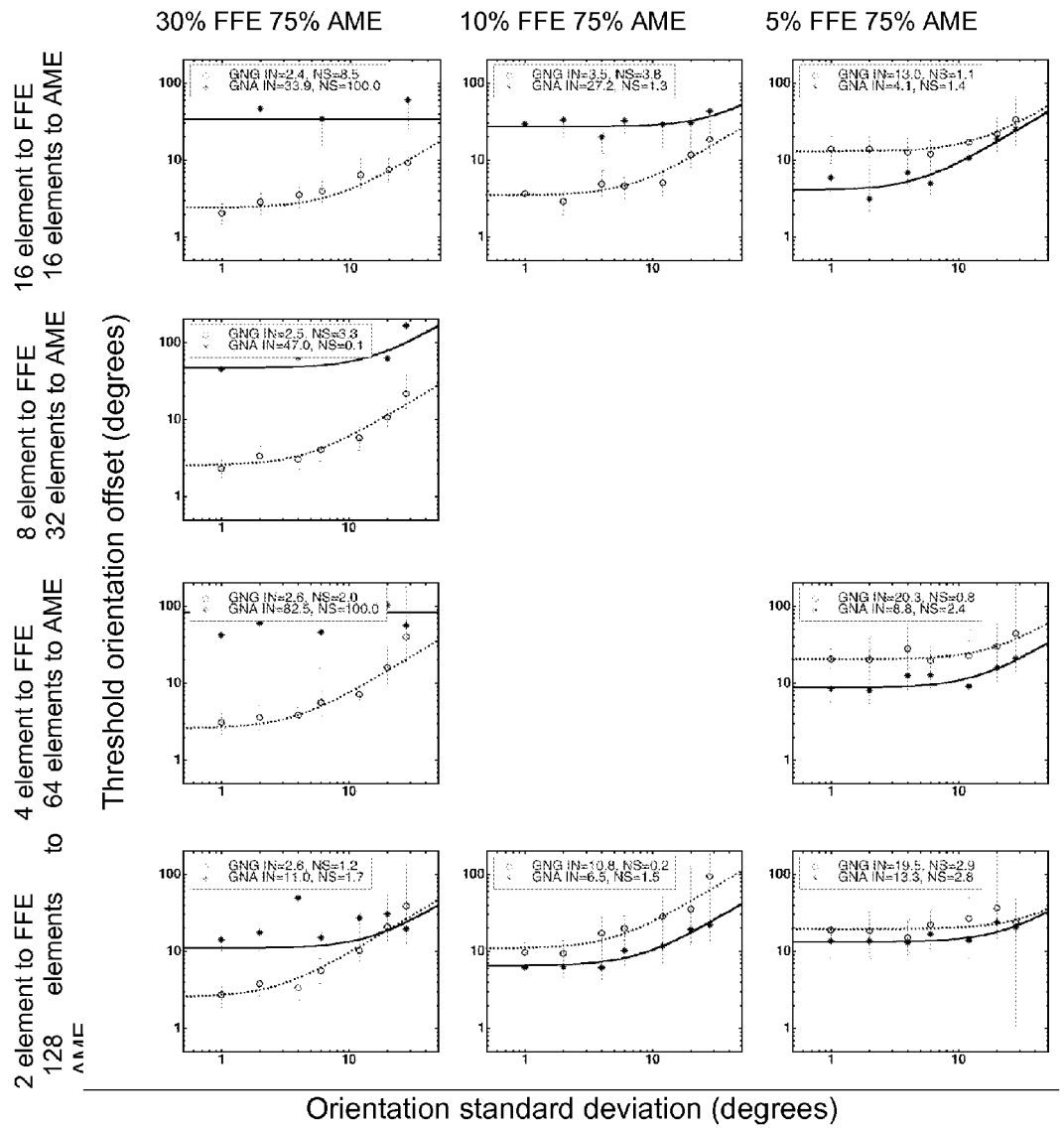

FIG. 14 shows combinations of different numbers of elements and contrast in one sample observer amblyope. FIG. 14(A) is the reference monocular condition where both eyes showed similar performances when 16 signal Gabors were presented to either of them with 30% contrast to FFE and 75% to AME. FIG. 14(B) shows the variations of number of samples and contrast and combination of the two. It is shown for this subject that changing each variable alone brings the performances of the two eyes close to each other but it is not enough (at least at the ranges applicants used) to equalize the performances. However when two variables were changed together, the performance of the two eyes became similar.

General Discussion

The results from Applicants' dorsal and ventral pathway investigation clearly demonstrate that under certain, 'balanced' conditions, the amblyopic visual system can support binocular interactions. The ratio of contrast that is required to each eye to achieve this balancing may also be considered as an objective measure of the amount of inter-ocular inhibition present in a particular patient's visual system. This contrast ratio which leads to binocular matched performances of AME and FFE cannot be predicted from a knowledge of the monocular contrast ratios, demonstrating that the suppression present in the amblyopic visual system needs to be measured individually when assessing AME function and also in clinical assessments of treatment outcomes. Highlighting this point is the current finding that AME monocular performances were influenced by whether the FFE was patched or unpatched and viewing mean-luminance grey. Therefore measures of AME function when the fellow eye is patched are almost certainly underestimating the visual deficits present in the AME under normal, binocular, viewing conditions.

Highlights of the Applicants' Study are:

Binocular interactions in amblyopia: Applicants have shown that in all the amblyopic observers tested, the binocular system, whilst weak was intact. This was true for both the dorsal and the ventral processing streams.

Implication of this method in treatment: Applicants' results have significant implications for the treatment of amblyopia. The fact that it is possible to artificially create conditions where AME has dominancy over FFE, is very important for treatment of amblyopia for two reasons. First, this shows it is possible to activate AME without any need to patch or penalize the FFE. Second, under these conditions the visual system fuses the information from two images presented to AME and FFE, which shows that the binocular system is active in amblyopia. Stereopsis, which is lost in most strabismic amblyopes, requires binocular vision and the fusing of images from the two eyes. Although activating the binocular system in amblyopes does not necessarily lead to stereopsis, training the amblyopic visual system binocularly, might restore the stereopsis in amblyopia, in spite of the evidence that shows that stereopsis improves even under monocular visual training i.e. patching (Mitchell, Howell & Keith, 1983).

Furthermore, there is evidence that some higher order functions in amblyopia are not developed, even for the FFE which has normal monocular vision. The loss of function in the FFE is hypothesized to be due to deficits in binocular function. Therefore, restoring binocular vision might help the amblyopic visual system restore such mechanisms.

REFERENCES

Baker, D. H., Meese, T. S., & Summers, R. J. (2007). Psychophysical evidence for two routes to suppression before binocular summation of signals in human vision. *Neuroscience*, 146 (1), 435-448.

Braddick, O. (1974). A short-range process in apparent motion. *Vision Res*, 14 (7), 519-527.

Brainard, D. H. (1997). The Psychophysics Toolbox. *Spatial Vision*, 10 (4), 433-436.

Campbell, F. W., & Green, D. G. (1965). Monocular versus binocular visual acuity. *Nature*, 208 (5006), 191-192.

Crawford, M. L., & von Noorden, G. K. (1979). The effects of short-term experimental strabismus on the visual system in *Macaca mulatta*. *Invest Opthalmol Vis Sci*, 18 (5), 496-505.

Edwards, M., & Badcock, D. R. (1995). Global motion perception: No interaction between the first- and second-order pathways. *Vision Research*, 35 (18), 2589-2602.

Foster, D. H., & Bischop, W. F. (1997). Bootstrap estimates of the statistical accuracy of thresholds obtained from psychometric functions. *Spatial Vision*, 11 (1), 135-139.

Harrad, R., Sengpiel, F., & Blakemore, C. (1996). Physiology of suppression in strabismic amblyopia. *Br J Opthalmol*, 80 (4), 373-377.

Hess, R. F., Hutchinson, C. V., Ledgeway, T., & Mansouri, B. (2007). Binocular influences on global motion processing in the human visual system. *Vision Res*, 47 (12), 1682-1692.

Hubel, D. H., & Wiesel, T. N. (1965). Binocular interaction in striate cortex of kittens reared with artificial squint. *Journal of Neurophysiology*, 28 (6), 1041-1059.

King-Smith, P. E., & Rose, D. (1997). Principles of an adaptive method for measuring the slope of the psychometric function. *Vision Research*, 37 (12), 1595-1604.

Kiorpes, L., Kiper, D. C., O'Keefe, L. P., Cavanaugh, J. R., & Movshon, J. A. (1998). Neuronal correlates of amblyopia in the visual cortex of macaque monkeys with experimental strabismus and anisometropia. *Journal of Neuroscience*, 18 (16), 6411-6424.

Levi, D. M., Pass, A. F., & Manny, R. E. (1982). Binocular interactions in normal and anomalous binocular vision: effects of flicker. *Br J Opthalmol*, 66 (1), 57-63.

Mansouri, B., Allen, H. A., Hess, R. F., Dakin, S. C., & Ehrt, O. (2004). Integration of orientation information in amblyopia. *Vision Research*, 44 (25), 2955-2969.

Mansouri, B., Hess, R. F., Allen, H. A., & Dakin, S. C. (2005). Integration, segregation, and binocular combination. *Journal of Optical Society of America A: Optics, Image Sciences, and Vision*, 22 (1), 38-48.

McKee, S. P., Levi, D. M., & Movshon, J. A. (2003). The pattern of visual deficits in amblyopia. *J Vis*, 3 (5), 380-405.

Meese, T. S., Georgeson, M. A., & Baker, D. H. (2006). Binocular contrast vision at and above threshold. *J Vis*, 6 (11), 1224-1243.

Mitchell, D. E., Howell, E. R., & Keith, C. G. (1983). The effect of minimal occlusion therapy on binocular visual functions in amblyopia. *Invest Opthalmol Vis Sci*, 24 (6), 778-781.

Newsome, W. T., Britten, K. H., Salzman, C. D., & Movshon, J. A. (1990). Neuronal mechanisms of motion perception. *Cold Spring Harb Symp Quant Biol*, 55, 697-705.

Newsome, W. T., & Pare, E. B. (1988). A selective impairment of motion perception following lesions of the middle temporal visual area (MT). *Journal of Neuroscience*, 8 (6), 2201-2211.

Pelli, D. G. (1997). The VideoToolbox software for visual psychophysics: transforming numbers into movies. *Spatial Vision*, 10 (4), 437-442.

Pelli, D. G., & Zhang, L. (1991). Accurate control of contrast on microcomputer displays. *Vision Research*, 31 (7-8), 1337-1350.

Rosenbach, O. (1903). Ueber monokulare Vorherrschaft beim binikularen Sehen. *Munchener Medizinische Wochenschriff*, 30, 1290-1292.

Sengpiel, F., & Blakemore, C. (1996). The neural basis of suppression and amblyopia in strabismus. *Eye*, 10 (Pt 2), 250-258.

Sengpiel, F., Blakemore, C., Kind, P. C., & Harrad, R. (1994). Interocular suppression in the visual cortex of strabismic cats. *J Neurosci*, 14 (11 Pt 2), 6855-6871.

Sengpiel, F., Freeman, T. C., & Blakemore, C. (1995). Interocular suppression in cat striate cortex is not orientation selective. *Neuroreport*, 6 (16), 2235-2239.

Vedamurthy, I., Suttle, C. M., Alexander, J., & Asper, L. J. (2007). Interocular interactions during acuity measurement in children and adults, and in adults with amblyopia. *Vision Res*, 47 (2), 179-188.

Watt, R. J., & Andrews, D. (1981). APE. Adaptive Probit estimation of the psychometric function. *Current Psychological Review*, 1, 205-214.

Wurtz, R. H., & Kandel, E. R. (2004). Motion and Form Perception. In: E. R. Kandel (Ed.) *Principles of Neuroscience* (p. 584).

The invention claimed is:

1. A binocular vision assessment and/or therapy apparatus comprising:
    a source of left eye image and right eye image pairs adapted to be viewed dichoptically, said pairs having a variable difference between said left eye image and said right eye image; and
    a dichoptic display system presenting a selected one of said images pairs as a right eye image to a patient's right eye and a left eye image to a patient's left eye, wherein said variable difference is adjustable to achieve binocular vision in a patient having a deficiency of binocular vision;
    wherein one image of said image pairs is information rich and another image of said image pairs is information poor.

2. The apparatus as claimed in claim 1, wherein said variable difference in information content is defined by a variable difference of signal and noise in said image pairs.

3. The apparatus as claimed in claim 1, wherein said image pairs relate to a motion discrimination task.

4. The apparatus as claimed in claim 1 wherein said image pairs relate to an orientation discrimination task.

5. The apparatus as claimed in claim 1, wherein said image pairs are composed of unstructured visual stimuli with comparable spatial or temporal properties.

6. The apparatus of claim 1 wherein a processor processes user input data obtained related to visual discrimination tasks to determine level of binocular vision.

7. The apparatus of claim 6 wherein said processor processes user input data obtained related to said tasks to determine level of binocular vision, said processor adjusts the information content presented to each eye before each task as a function of user input related to performance at the preceding task.

8. The apparatus of claim 6 wherein said assessment of binocular vision allows said processor to adjust the information content presented to the weaker eye in a manner which is inversely proportional to the level of binocular vision.

9. The apparatus as claimed in claim 1, wherein said source comprises: a processor for processing a digital image into said first information rich image and said second information poor image, said processor providing a set of images that correspond to a range of different ratios of information between said first and said second images in accordance with at least one input attribute value corresponding to said variable difference.

10. The apparatus as claimed in claim 9, wherein said processing separates said digital image into said first information rich image and said second information poor image, wherein said second image contains complementary information to said first image.

11. The apparatus as claimed in claim 1, wherein said source comprises a data store of said image pairs having a variety of differences in information content, and said variable difference is selected by selecting image pairs from said data store.

12. The apparatus of claim 1, comprising a user input device for adjusting said variable difference.

13. The apparatus of claim 1 comprising a user input device for selecting a response in a binocular vision task.

14. The apparatus of claim 1 wherein said dichoptic display comprises LCD shutter glasses connected wirelessly to a computer containing software for executing a treatment regimen.

15. The apparatus of claim 1 which is adapted for integration into a standard binocular apparatus of an eye specialist.

16. The apparatus of claim 1, adapted to record over time a value representing said variable difference at which said patient was able to achieve binocular vision.

17. The apparatus of claim 16 wherein said apparatus comprises a display for displaying a representation of said value over time.

18. A method of assessing a level of binocular vision comprising:
 (a) providing to a patient a binocular vision assessment apparatus that includes
  a source of left eye image and right eye image pairs adapted to be viewed dichoptically, said pairs having a variable difference in information content between said left eye image and said right eye image, and wherein one image of said image pairs is information rich and another image of said image pairs is information poor and
  a dichoptic display system that presents a selected one of said image pairs as a right eye image to the patient's right eye and a left eye image to the patient's left eye, wherein said variable difference in information content is adjustable to achieve binocular vision in a patient having a deficiency of binocular vision;
 (b) receiving input from the patient regarding patient perception of said presented images;
 (c) adjusting said variable difference in information content between said right eye and left eye images as a function of said patient input; and
 (d) assessing the level of binocular vision based on a value of said variable difference.

19. The method as claimed in claim 18 wherein said variable difference in information content is defined by a variable difference of signal and noise in said image pairs.

20. A method of improving binocular vision in a patient comprising;
 (a) providing to a patient a binocular vision treatment apparatus that includes
  a source of left eye image and right eye image pairs adapted to be viewed dichoptically, said pairs having a variable difference in information content between said left eye image and said right eye image, and wherein one image of said image pairs is information rich and another image of said image pairs is information poor and
  a dichoptic display system that presents a selected one of said image pairs as a right eye image to the patient's right eye and a left eye image to the patient's left eye, wherein said variable difference in information content is adjustable to achieve binocular vision in a patient having a deficiency of binocular vision;
 (b) instructing said patient to perform at least one dichoptic task using said presented one of said image pairs;
 (c) adjusting said variable difference in information content and determining a difference necessary to achieve binocular vision in said patient; and
 (d) basing further therapy on said difference.

* * * * *